United States Patent [19]
Frankel et al.

[11] Patent Number: 5,637,458
[45] Date of Patent: Jun. 10, 1997

[54] APPARATUS AND METHOD FOR THE DETECTION AND ASSAY OF ORGANIC MOLECULES

[75] Inventors: Robert Frankel, Rochester; James M. Forsyth, Macedon, both of N.Y.

[73] Assignee: Sios, Inc., Macedon, N.Y.

[21] Appl. No.: 278,033

[22] Filed: Jul. 20, 1994

[51] Int. Cl.⁶ ................................. C12Q 1/68
[52] U.S. Cl. ............... 435/6; 435/7.1; 436/527; 436/164; 436/149; 436/807; 422/55; 422/57; 422/82.01; 422/82.05; 356/318; 356/244
[58] Field of Search ............ 435/6, 7.1, 8; 422/55, 422/57, 82.01, 85.05, 82.09; 436/149, 164, 165, 172, 174, 177, 178, 805, 806, 807, 518, 524, 527, 535; 356/318, 345, 244, 246

[56] References Cited

U.S. PATENT DOCUMENTS

| | | | |
|---|---|---|---|
| 3,397,278 | 8/1968 | Pomerantz | 257/650 |
| 3,539,262 | 11/1970 | Pryor | 356/361 |
| 3,572,948 | 3/1971 | Catherin | 356/434 |
| 3,680,963 | 8/1972 | Edwards et al. | 356/349 |
| 4,097,153 | 6/1978 | Dehemigis | 356/103 |
| 4,289,403 | 9/1981 | Allington | 356/361 |
| 4,447,153 | 5/1984 | Cremers et al. | 356/361 |
| 4,477,187 | 10/1984 | Pettit et al. | 356/335 |
| 4,737,464 | 4/1988 | McConnell et al. | 436/43 |
| 4,860,304 | 8/1989 | Mooradian | 372/92 |
| 4,909,990 | 3/1990 | Block et al. | 422/82.11 |
| 4,912,530 | 3/1990 | Bessho | 356/349 |
| 4,982,405 | 1/1991 | Zayhowski et al. | 372/10 |
| 4,984,903 | 1/1991 | Sweeney | 374/123 |
| 5,153,669 | 10/1992 | Degroot | 356/349 |
| 5,159,408 | 10/1992 | Waldenmaier et al. | 356/357 |
| 5,194,133 | 3/1993 | Clark et al. | 204/608 |
| 5,198,369 | 3/1993 | Itoh et al. | 436/534 |
| 5,296,375 | 3/1994 | Kricka et al. | 435/2 |
| 5,483,469 | 1/1996 | Van Den Engh et al. | 364/555 |

OTHER PUBLICATIONS

Fodor et al., Copyright American Association for The Advancement of Science, Feb. 1991, pp. 2–12.
Burlatsky et al., Influence of Solid Friction on Polymer Relaxation, Etc., Jun. 1993, p. 1782–1784.
Viovy et al., Irreversible Trapping of DNA During Crossed-Field Gel Electrophoresis, 1992, pp. 2–5.
Chu, Laser Manipulation of Atoms and Particles, Aug. 1991, pp. 861–866.

*Primary Examiner*—Paula K. Hutzell
*Assistant Examiner*—Rachel Heather Freed
*Attorney, Agent, or Firm*—Harris Beach & Wilcox, LLP

[57] ABSTRACT

A system for biomolecular separation and detection of a molecular species includes a solid state laser detector having a sample channel therein. The presence of a molecular species is indicated by a frequency shift in the laser's output, which is detected by optical heterodyning the laser's output with the output of a reference laser. The interior of the sample channel is optionally coated with a ligand for binding the molecular species of interest. The system involves preprocessing a sample by electroosmotic separation in channels that are lithographically formed in a two-dimensional planar substrate. Molecular separation is also accomplished in a nanostructural molecular sieve comprising spaced apart posts defining narrow channels therebetween.

32 Claims, 14 Drawing Sheets

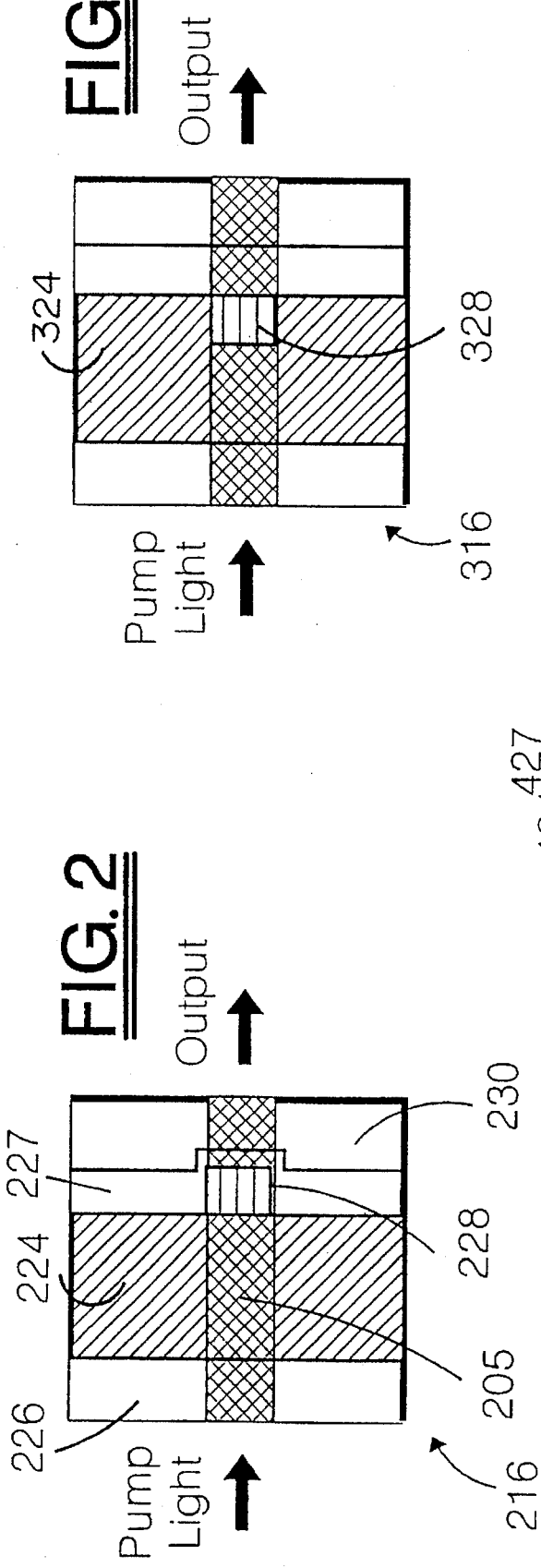

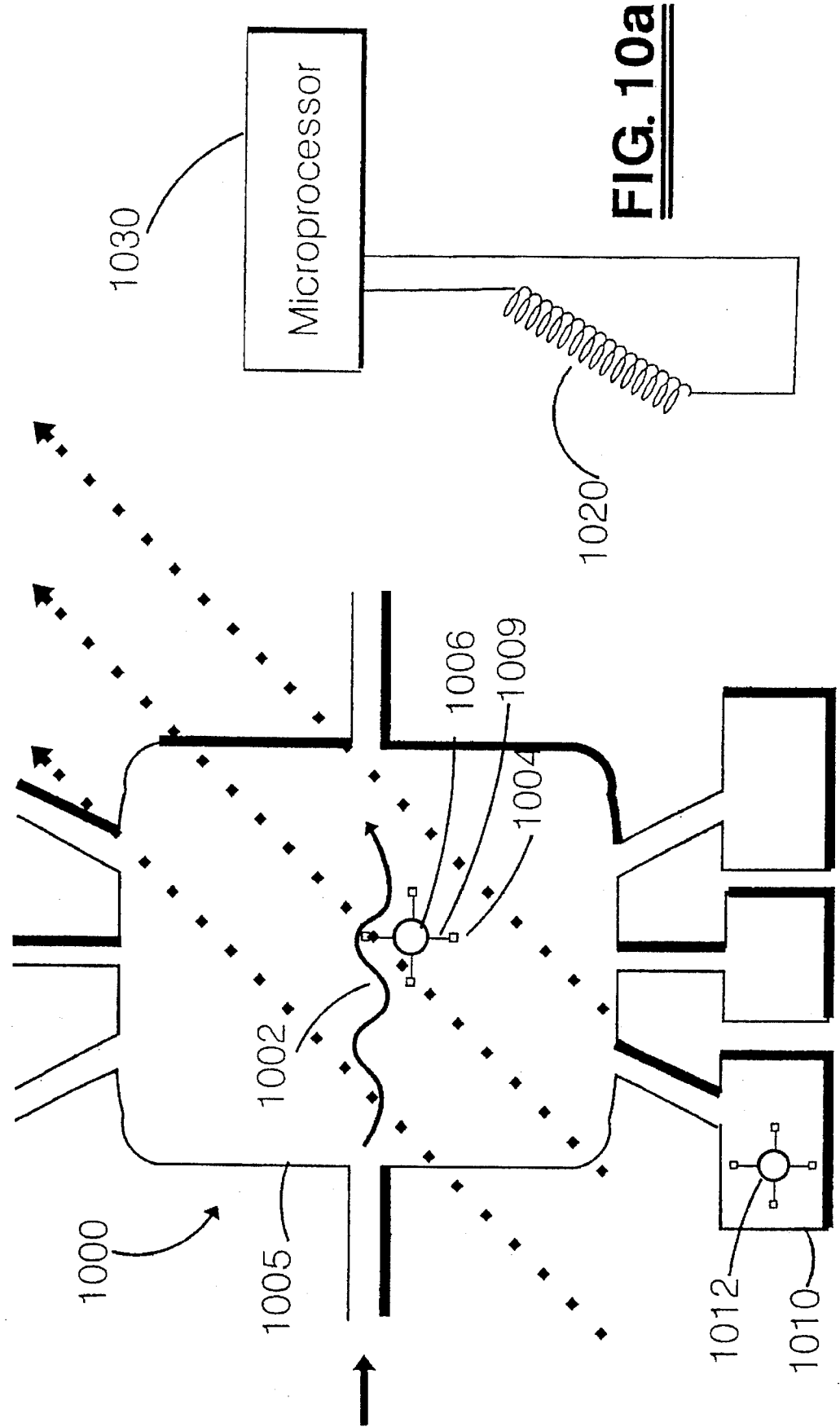

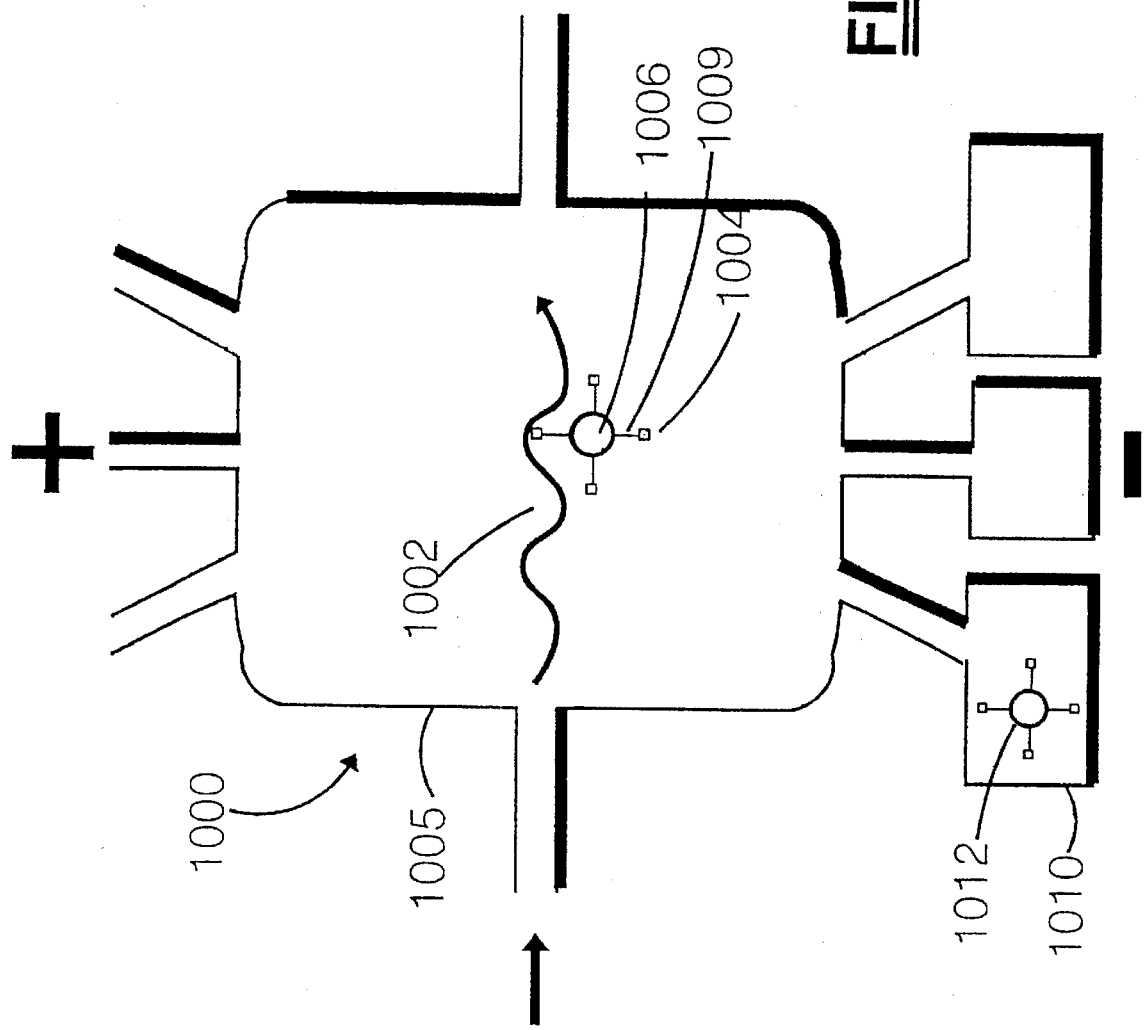

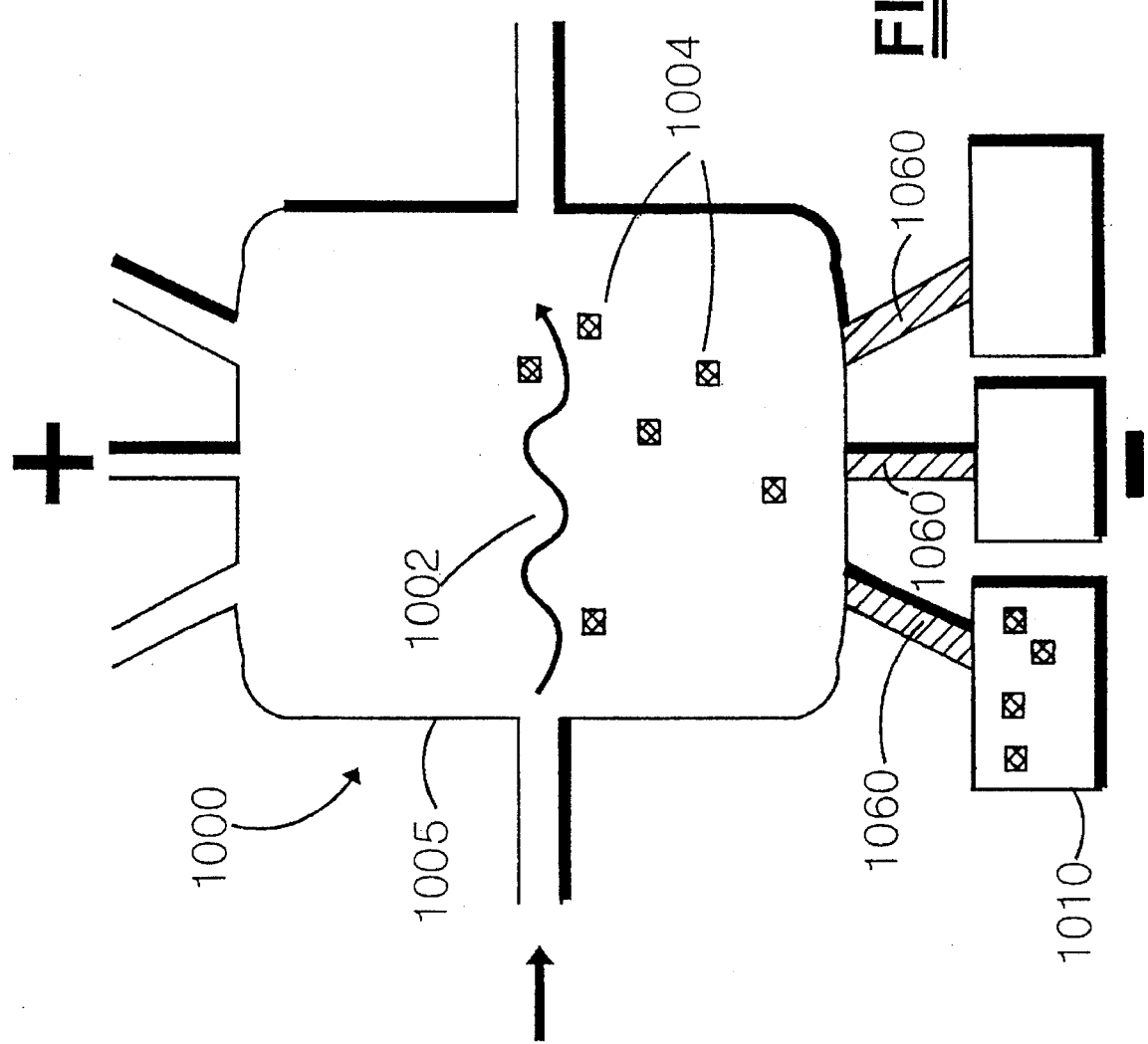

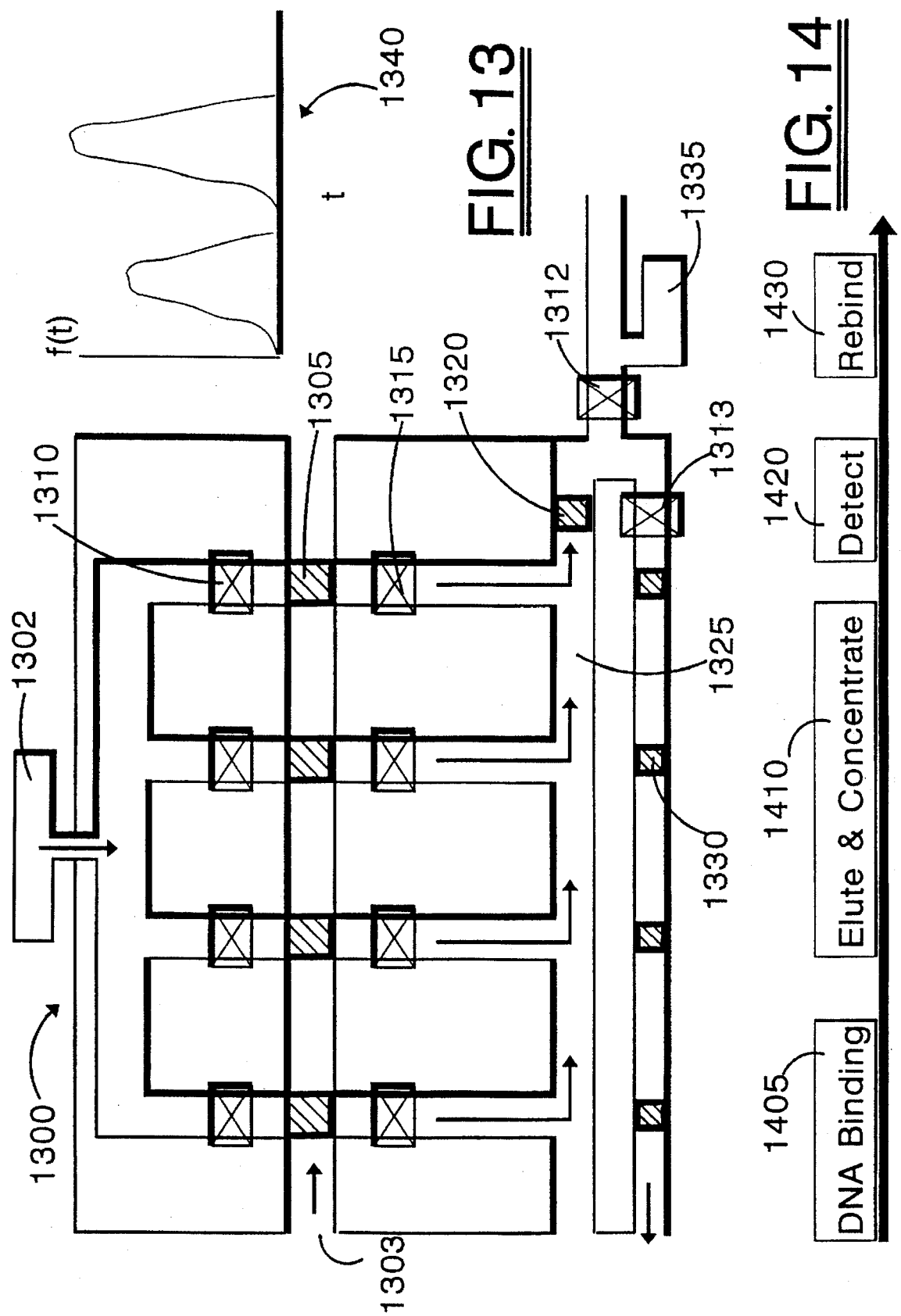

APPARATUS AND METHOD FOR THE DETECTION AND ASSAY OF ORGANIC MOLECULES

BACKGROUND OF THE INVENTION

1. Field of the Invention

This invention relates to the quantitative separation and detection of organic molecules. More particularly this invention relates to systems for separating a species of organic molecules, and for detecting and quantifying the separated molecular species with a continuous wave laser through which the separated organic molecular species is conveyed.

2. Description of the Prior Art

An extensive range of both industrial and clinical processes are based on determination of the identities and concentrations of organic molecules in solution. Primary samples obtained for analysis may range from industrial fermentation processes to the bodily fluids of animals or humans. These samples typically contain a very wide range of molecules and molecular complexes in an equally wide range of concentrations. To deal with this a typical assay system will consist of six fundamental parts: sample collection, sample filtration, molecular separation, molecular recognition, concentration measurement, and data analysis and presentation. Not all assays require all six steps; for example, filtration is often not required. However, separation, recognition, and concentration measurement are usually in the critical path to data analysis. The present invention provides a novel and greatly improved methodology to this critical path activity.

Chemical and biochemical separation technologies have been extensively developed over the past 100 years. A complete review of all separation technologies is beyond the scope of this application. However, it is useful to review some of the most common separation technologies and to compare and contrast them to the invention disclosed here.

Two of the most common separation technologies in current application are electrophoresis and chromatography. Electrophoresis refers to the migration of charged molecules or ions in a liquid medium under the influence of an applied electric field. This is also known as electroosmosis. Chromatographic separations operate by introducing a sample into a flowing stream of gas or liquid that passes through a bed of support particles. The support particles are known as the stationary phase and the flowing stream is known as the mobile phase. The driving force for chromatic separations may be fluid or gas pressure, gravity, or capillary action.

Both electrophoresis and chromatography have many embodiments. Electrophoretic separations are used to analyze and characterize proteins and nucleic acids, especially DNA and RNA. Chromatography is often used to isolate specific molecules and characterize smaller molecules such as drugs and amino acids. Although the inventions described in this disclosure can be used in both types of separations, they find greater application in electrophoresis than chromatography. Therefore we will describe present electrophoretic practice in greater detail.

The first electrophoresis method used in the study of proteins was the moving boundary method devised by Tiselius in 1937 which was a fully fluid electrophoretic system. Presently, most electrophoretic separations are carried out in a porous support medium such as cellulose paper, agarose, and polyacrylamide gel films. This is called zone electrophoresis. A related technique called capillary electrophoresis uses electroosmotic flow separation in 50–100 µm capillary placed in very strong electric fields to separate molecules, with or without the use of a porous matrix.

Molecular electrophoretic separation technology used in practice today takes advantage of separation by both electroosmosis and molecular sieving. Electroosmosis alone may be used to separate biomolecules. However, electroosmotic separations require longer separation distances—up to a meter or more—and additionally require 10–20 kilovolt potentials along the electrophoretic length. Presently, only capillary electrophoresis is performed this way. In slab geometries, meter long separations are impractical, and 20 kilovolt potentials can lead to excessive heating and electronic arcing problems. Therefore, gels are introduced to act as molecular sieves to enhance molecular separations. Gels provide quicker separations in smaller distances and use lower voltages. Almost all molecular sieves used in separations are gel polymerized molecules from poured or cast solutions. Sieve pore sizes may range from 0.5 µm in agarose gels (designed to separate large DNA fragments) to 0.01 µm for polyacrylamide gels used to separate standard protein mixtures.

The rate of migration of a charged particle in a solution is a function of five variables. These include 1) the net electrical charge of the molecule (which is a function of the pH of the buffer solution), 2) the size and shape of the molecule, 3) the electric field strength, 4) properties of the support medium (e.g. pore size and fixed charges), and 5) the temperature of operation.

The net electrical charge on a molecule is a strong function of the pH of the buffer medium. The separation method known as isoelectric focussing separates amphophilic molecules (molecules possessing both positive and negative charges) such as proteins, by their migration in stable pH gradient. The protein moves to the zone in the medium where the pH is equal to the isoelectric point of the protein.

As opposed to isoelectric focusing, most electrophoretic procedures result in the separation of molecules by molecular weight. Under these circumstances, separation is accomplished by the sieving properties of the gel support medium or matrix. Smaller molecules move faster than larger molecules in appropriately sized gels. To aid in providing a strict molecular weight separation, protein molecules are often denatured in a detergent such as sodium dodecyl sulfate (SDS) to remove the effects of tertiary and quaternary structure on molecular mobility. For separation of standard proteins of molecular weight from 200,000 to 10,000 daltons a 7.5% polyacrylamide gel may be used to provide a pore size down to 5 nanometers (50 Angstroms). Most gel systems rarely resolve more than 100 bands of protein.

In order to enhance the number of electrophoretically resolvable bands, O'Farrell in 1975 introduced the method of two-dimensional (2D) electrophoresis. In this technique charge dependent isoelectric focussing is used in the first separation axis. After separation, the one-dimensional gel is extruded from the gel tube and placed in contact with a thin polyacrylamide gel slab that incorporates SDS. At the end of the process the polypeptides are detected, usually by chemical staining or autoradiography. 2D gels allow the simultaneous visual detection of more than 1000 peptides. Thus they are often used in cell or organ "fingerprinting" applications.

Immunologic techniques are often combined with electrophoretic separations to provide powerful diagnostic tools. In immunoelectrophoresis, nondenatured proteins are separated on an agarose gel. The method of applying the antibody to the separated mixture often determines the class of immunoelectrophoretic technique being used. In standard immunoelectrophoresis, the antibody is applied to a trough next to the separation medium and both antigens and antibodies are allowed to diffuse into each other, forming arcs of immunoprecipitates. In crossed immunoelectrophoresis, a second dimension of electrophoresis is used to drive the antigens into an antibody coated gel, while in immunofixation, antibody is spread over the gel and non-precipitated proteins are washed away.

Often the amount of antigen present in a separation medium is insufficient for detection in a gel matrix. To overcome this limitation proteins are often transferred to a solid phase such as nitrocellulose paper where either radioactive isotopes or enzymatic assays of greater sensitivity can be applied. This procedure is called Western blotting.

Small, single stranded DNA fragments are separated under denaturing conditions on polyacrylamide gels. Larger, double stranded molecules can be separated in more porous agarose gels. However, duplex DNA longer than 20 kilobase pairs cannot be separated in a size-dependent manner in a one-directional electric field. This is related to the way the long DNA molecules move through the pores of the gel. They are probably elongated in the direction of the field, and may wrap around the agarose gel matrix and become immobilized. Thus the DNA molecules must be made to continually reorient if they are to move through the gel. To accomplish reorientation, pulse-field electrophoresis has been developed. Here two nonhomogeneous, mostly perpendicular fields are applied to the separating DNA mixture. One field causes the separation while the other promotes reorientation. The newest systems optimize the angle between the two fields. Pulse times are generally of the order of a minute. To separate large DNA fragments, gel pore sizes of up to 0.2–0.5 μm are used.

Capillary electrophoresis is a recent variation on the traditional slab gel electrophoretic techniques. Here many of the standard techniques such as zone electrophoresis, isoelectric focussing, and gel electrophoresis are carried out in 25–75 μm fused silica capillary about 100 cm long. The capillary is connected to a high voltage supply on one end and a detector and/or fraction connector on the other end. The advantages of performing electrophoretic separations in capillaries include improved heat dissipation (which allows use of steeper potential gradients and hence, faster separations), reduced sample volume requirements, reduced zone (or protein band) broadening, and easier process automation. Sample volumes are kept in the picoliter or nanoliter range in order to maintain the buffer-electrolyte to solute concentration ratio of at least $10^3$, which minimizes distortion in the applied field caused by the presence of the sample.

Many detection schemes are possible for detection of the electrophoresing sample at the end of the capillary tube. These include optical absorption and fluorescence, radiometric, and mass spectrometer means. With the most sensitive methods as little as $10^{-20}$ moles of substance can be detected.

Most recently it has been shown by groups at the University of New Mexico (UNM) and at Ciba-Geigy Labs that it is possible to perform electroosmotic amino acid separations in lithographically patterned channels etched into a glass substrate. These channels function in a similar manner to capillaries used in electrophoresis. The UNM microseparations were extremely rapid (as short as 4 seconds) and required little material. This is the first step toward building full capillary-type electrophoretic separation systems on a planar substrate, or chip. Attempts are now being made to form miniature, multistage separation and analysis systems using semiconductor technology, that incorporate electrically active substrates for separation channel switching. However, there are limitations in performing electroosmotic separations on active semiconductor substrates. Electrical potential differences in the multikilovolt range are extremely difficult to maintain in integrated circuits. In addition, meter long separations required for large biomolecule separations demand large planar areas, even if spiral winding of the channel is employed.

All existing electrophoretic systems have limitations and drawbacks which we will now discuss. Identification of the separated molecules is a major issue in most applications of electrophoresis. There are two basic types of molecular identification systems in use. In one case the electrophoretic process is stopped while all molecules are still in the electrophoretic medium resulting in the formation of an electrophoretogram. The separated, arrayed molecules are detected in parallel by chemical staining to reveal their presence, or by measuring a physical property of the molecules, such as fluorescence or the effects from radioactive labelling. This type of detection system is common in protein and DNA slab gel electrophoresis.

In the other system the molecules are detected as they sequentially exit the electrophoretic system. Detection may be by optical absorption, fluorescence, or radioactivity. This method is normally used to detect the results of capillary electrophoretic separations.

The Western blot methodology described above is a hybrid of these two methods, where the proteins of interest are transferred from the electrophoretogram to another solid support for readout.

Key issues in all detection systems include the dynamic range, sensitivity, specificity, calibration, and time to result. These issues will be examined in order here.

Electrophoretic systems separate molecules by their unique directed motions in an electric field. It is often desired to measure the quantity of a rare molecule which has drifted a distance extremely close to that of a substantially more abundant molecule. Methods to accomplish this include 2-dimensional electrophoresis (described above), use of a specific label (such as an antibody), or isolating the desired region of the gel or liquid fraction and reelectrophoresing this portion of the sample. To sharpen the electrophoretic zone structure, thinner gels, longer electrophoretic paths, and steeper voltage gradients are resorted to. As yet there has been no attempt to provide active feedback to sharpen electrophoretic bands.

Another challenge is to find the appropriate gel concentration to resolve both high molecular weight (>500,000 daltons) and low molecular weight components on a single separation. This may be dealt with by application of a discontinuous gel with two or more concentrations, or by use of a gradient gel system. Again, there has been no attempt reported to provide active, separate modulation of the high and low molecular weight regions after separation.

Sensitivity is a strong function of the stain used to report the presence of macromolecules. Clearly fluorescence staining with specific ligands is substantially more sensitive than standard absorption stains (such as Coomassie Brilliant Blue). However, fluorescent detection systems (which often require an ultraviolet or argon ion laser excitation source) are generally more expensive and slower in readout of electrophoretograms. Typical slab gel systems operate with several hundred micrograms of sample material. Capillary electrophoretic systems can operate with nanograms of sample. Detection thresholds can be exceptionally low if fluorescent or radioactive stains are used. Amounts as low as $10^{-20}$ moles can be detected in a given eluted fraction. Absorption measurements are usually carried out in the ultraviolet region, where proteins and nucleic acids are strongly absorptive. It is desirable to have a detector system which uses an inexpensive, long lived light source, and which has sensitivity in the sub-nanogram range.

Most gel systems are cast or poured from a solution. Variations in component concentrations, room temperature, buffer strengths, etc., can lead to variable drift rates. In slab gels the solvent front often does not move uniformly, creating a variation in separation distances across the slab or distorted bands within the gel. This can arise from excessive drying of the gel or from overapplication of the sample. In capillary electrophoresis, capillary bore variations as well as variations in the above mentioned parameters will create variations in elution time. System calibration is possible either by adding monitor substances to the elution channel, or by providing a separate lane for electrophoresing standard molecules of known molecular weight. Calibration can be enhanced with automated densitometric readout to provide curve fitting of lane electrophoretic separations and digital processing of electrophoretograms to remove run time variations. Nevertheless, any approach that will enhance reproducibility represents a major advance.

Many electrophoretic separations require 1 hour or longer. To this must be added gel preparation time, stain time, and readout time. An entire separation procedure may require 4–6 hours from start to finish. Additional time is required if enhanced resolution is needed, due to the use of longer gels and longer run times. Electrophoresis can be a rate limiting step in data delivery in both research and clinical applications. It would be highly desirable to have an electrophoretic medium that is reusable, precalibrated, and permits higher resolution, while providing shorter run times, active readout, and good end point detection. Reduction of the entire process to less than 30 minutes is a highly desirable goal in many areas of clinical practice, as results could be provided during the patient's diagnostic visit.

Quantitative molecular detection is a also key part of any chemical assay system. Electrochemical means may be employed using ion specific electrodes or biosensors to measure molecular concentrations directly. Such devices exhibit micromolar sensitivity, and are available for a limited number of molecules.

Direct optical detection relies upon fluorescence or absorption measurements; concentration is assessed by the strength of the signal. Not all molecules of interest have an adequate direct optical signature, however. Concentrations of macromolecules such as enzymes in solution (e.g. blood plasma) are difficult to measure directly this way.

A broader methodology of detection involves the use of a so-called "reporter" molecule. In this method the molecule of interest is brought into contact with a reagent which binds to the molecule and provides its own measurable signature. One such signature is a change in the optical absorbance of the reporter molecule. The rate of change of this signal is directly related to the concentration of the molecule. A wide range of such spectrophotometric systems have been developed and sold. Concentrations in the nanomolar range can be measured this way. Careful control of reagent concentration and purity is required to obtain accurate results.

The reporter molecule is sometimes a radioactive "tag" attached to the molecule of interest. Concentration is derived directly from the strength of the radioactive signal. Proper storage, handling, and disposal of the requisite radioactive materials is a general area of concern in the health care field.

In some cases fluorescent tags may be attached instead. Such tags usually require ultraviolet excitation. Some molecules are unstable under such actinic irradiation so this method is not universally applicable.

A new class of research instrument has appeared on the market which measures the real-time binding kinetics of label-free biomolecules. These systems all use the behavior of light reflection at the near grazing angle boundary of different refractive indices as a detection modality when the molecule of interest binds to a specific ligand attached to the optical surface. This phenomenon is known as frustrated total internal reflection (FTIR), and systems based on it have demonstrated an ability to detect molecular concentrations approaching the nanomolar level in some test conditions.

SUMMARY OF THE INVENTION

It is therefore a primary object of the present invention to provide a system of quantitative molecular detection that offers detection sensitivity below the 0.1 picomolar range, and eliminates the use of reporter molecules.

It is another object of the present invention to provide a system of molecular detection that greatly reduces the volume of sample required, and can be adapted to the requirements of industrial or clinical on-line process control.

It is yet another object of the present invention to provide a system of quantitative molecular detection that is readily adapted to parallel analysis of arrays of binding ligands.

It is still another object of the present invention to employ semiconductor fabrication technology in the generalized fabrication of biomolecular separation systems with the attendant benefits of miniaturization and scalability to mass production.

These and other objects of the present invention are attained by an apparatus for the identification of a molecular species in a fluid comprising a first laser having a plurality of reflective optical layers and a laser material disposed therebetween, and having photonic energy traveling therethough for interaction therewith to produce a coherent output. A sample chamber is disposed in the first laser and is traversed by the photonic energy, the chamber having an inlet for receiving a fluid and an outlet for discharging effluent. The laser output undergoes a frequency shift when a molecular species in the fluid enters the sample chamber therewith. The first laser can be a solid state microlaser.

In accordance with one aspect of the invention a detector of the frequency shift comprises a second laser for producing a reference output. A heterodyning means coupled to the first laser and the second laser produces a signal representative of a frequency difference between the output of the first laser and the reference output of the second laser.

In accordance with another aspect of the invention the fluid is an aqueous solution.

In accordance with another aspect of the invention the sample chamber is disposed in the laser material, or proximate the reflective optical layer.

In accordance with yet another aspect of the invention an affinity coating is disposed on an interior surface of the sample chamber for binding with the molecular species.

In accordance with still another aspect of the invention a microlens is disposed in the first laser for converging the photonic energy onto a small region of the sample chamber, the affinity coating being disposed substantially on the region.

In another form of the invention, the laser detector is combined in a system for the identification of a molecular species in a fluid which comprises a means for separating a molecular species of interest from another molecular species. The means for separating comprises a molecular sieve comprising a plurality of nanostructures, the nanostructures comprising spaced apart posts defining channels therebetween for passage therethrough of molecules. The nanostructures are fabricated on a planar substrate that further comprise a cover plate that forms a roof over the channels. The molecular sieve has a pore size of 0.5–0.02 μm.

The system further comprises a recorder for recording the signal of the heterodyning means as a function of time, whereby an interval that is initiated by an introduction of a molecular species into the means for separating and is terminated by a presence of the molecular species in the sample chamber can be measured.

In yet another form of the invention a system is adapted for the analysis of chromosomes of the type that accepts chromosomes that have been isolated from a cell and comprises a network of electroosmotic channels formed on a planar, two-dimensional substrate having an inlet for receiving a chromosome in a fluid environment; control means for directing the chromosome along a desired path through the network, whereby a first chromosomal species can be separated from a second chromosomal species.

In another aspect of the invention the network of channels comprises a plurality of spaced apart posts defining a plurality of intersecting channels therebetween, the channels having a width dimension between about 10 microns and 50 microns and a first electrode disposed at a first intersection of the channels. Electrical potentials appear on the first and second electrodes. The system includes a control to adjust the electrical potentials and the gradient therebetween, so that the chromosome can be directed from the first intersection to the second intersection.

In accordance with another aspect of the invention the posts form a diamond array.

In accordance with still another aspect of the invention the network comprises: a branching network of electroosmotic channels, having a plurality of branch points, each the branch point being guarded by a microvalve that is selectable between an open position and a closed position; and means for controlling the microvalves; whereby the chromosome can be directed along a selected one of a first arm and a second arm of the branch point.

In accordance with a further aspect of the invention the system comprises a microreaction pulse chamber coupled to the outlet of the sample chamber. It has a first chamber for receiving the chromosome, and a second chamber for containing a reactant for reaction with the first chromosomal species; and is furnished with means for cyclically deploying the reactant from the second chamber into the first chamber into contact with the first chromosomal species and thereafter returning the reactant into the second chamber.

In accordance with another aspect of the invention the reactant is attached to a solid support containing a magnetic material therein, and the means for cyclically deploying the reactant comprises a pulsed reversible magnetic field generator.

In accordance with another aspect of the invention the means for cyclically deploying comprises an optical tweezer.

In accordance with yet another aspect of the invention the reactant is unbound, and the means for cyclically deploying comprises a generator means for producing a reversing electroosmotic field in the pulse chamber; and a molecular sieve formed on a two dimensional substrate which allows passage therethrough of the reactant and does not allow passage therethrough of the chromosome.

The invention provides an integrated system for organic molecular separation and detection. It consists of planar microstructures for separation coupled to a unique, miniaturized, laser based detection system. The planar microstructure is an electrophoretic channel containing a two dimensional nanostructure which acts as a molecular sieve. Typical sieve pore sizes range from 0.5–0.02 μm. This arrangement greatly enhances the molecular separation per unit channel length and reduces the time and potential required to effect separation. The detector subsystem is also fabricated in a planar geometry, allowing it to be conveniently coupled to the separation subsystem. The laser detector may be configured in two different ways. One embodiment is adapted to detect the presence of the molecular bands in an electrophoretic separation system, while the other embodiment is optimized to perform concentration measurements for specific ligands.

The electrophoretic separation system is built on a semiconductor or glass substrate, preferably using lithographically defined posts to provide electrophoretic molecular sieving action. While such structures have previously been used to obstruct molecular flow, the inventors believe that the use of such structures as a separation medium has not been heretofore achieved or suggested. The lithographically defined molecular sieving structures may range in size from 0.5 μm to 0.02 μm or less. Such structures may be fabricated using a variety of conventional techniques, such as optical lithography, deep UV holography, X-ray lithography, or particle beam lithography. Ultrasmall channels may be fabricated by biased photoresist development, while high aspect ratios may be achieved by pattern transfer and anisotropic etching (e.g. reactive ion etching). The matrix of columnar structures may be regular, discretized to provide multiple sized separation regions, or continuously graded along the direction of separation. Many separate and parallel electrophoretic separation lanes may be generated to create the equivalent of a multilane slab gel. Alternatively, a large 2-dimensional grid of nanostructures may be created. In this case, electrophoretic lanes may be defined by placing the separation channel in an electronically defined potential well that prevents specific charge flow orthogonal to the direction of separation.

Such a separation medium is physically different from a gel, which is a random, three dimensional polymer network with a stochastic pore size distribution. Lithographically defined solid state sieves also differ from gel based sieves in that they provide sieving in only one of the two axes orthogonal to the direction of flow. This difference in sieving action is especially pronounced in the case of rod shaped molecules undergoing separation. We disclose here three techniques to facilitate the sieving of separating molecules by the above noted lithographically formed two dimensional solid state matrix:

1. A pulsed electric field is employed to reorient the molecules as they flow through the sieve;

2. A magnetic field is applied to orient molecules with a dipole moment. The dipoles precess around the magnetic field axis to effect reorientation; and 3. The physical barriers in the solid state matrix have different heights in the separation region to cause turbulent flow and effect reorientation.

The addition of lithographically defined obstacles to electroosmotic flow has several advantages. These include lower voltage requirements for separation, finer separations in shorter distances, enhanced batch-to-batch reproducibility in use of the electrophoretic medium, ability to perform multistep separations on a single semiconductor substrate, ability to use extremely small sample volumes for separations, and reusability of the medium.

The detector consists preferably of a continuous wave (CW), single frequency laser containing a thin, transparent, planar sample chamber inside the laser cavity.

BRIEF DESCRIPTION OF THE DRAWING

For a better understanding of these and other objects of the present invention, reference is made to the detailed description of the invention which is to be read in conjunction with the following drawings, wherein:

FIGS. 2–4 are sectional views of alternate embodiments of a laser detector in accordance with the invention;

FIGS. 10a–10d are schematic views of a pulse chamber formed on a two-dimensional substrate for the pulsed reaction of DNA with a reactant;

FIG. 13 is a schematic diagram of a system of DNA probe chambers suitable for the analysis of DNA fragments in accordance with the invention;

FIG. 14 is a diagram that is helpful in understanding the operation of the system of FIG. 13.

DESCRIPTION OF THE PREFERRED EMBODIMENT

Figure 1:
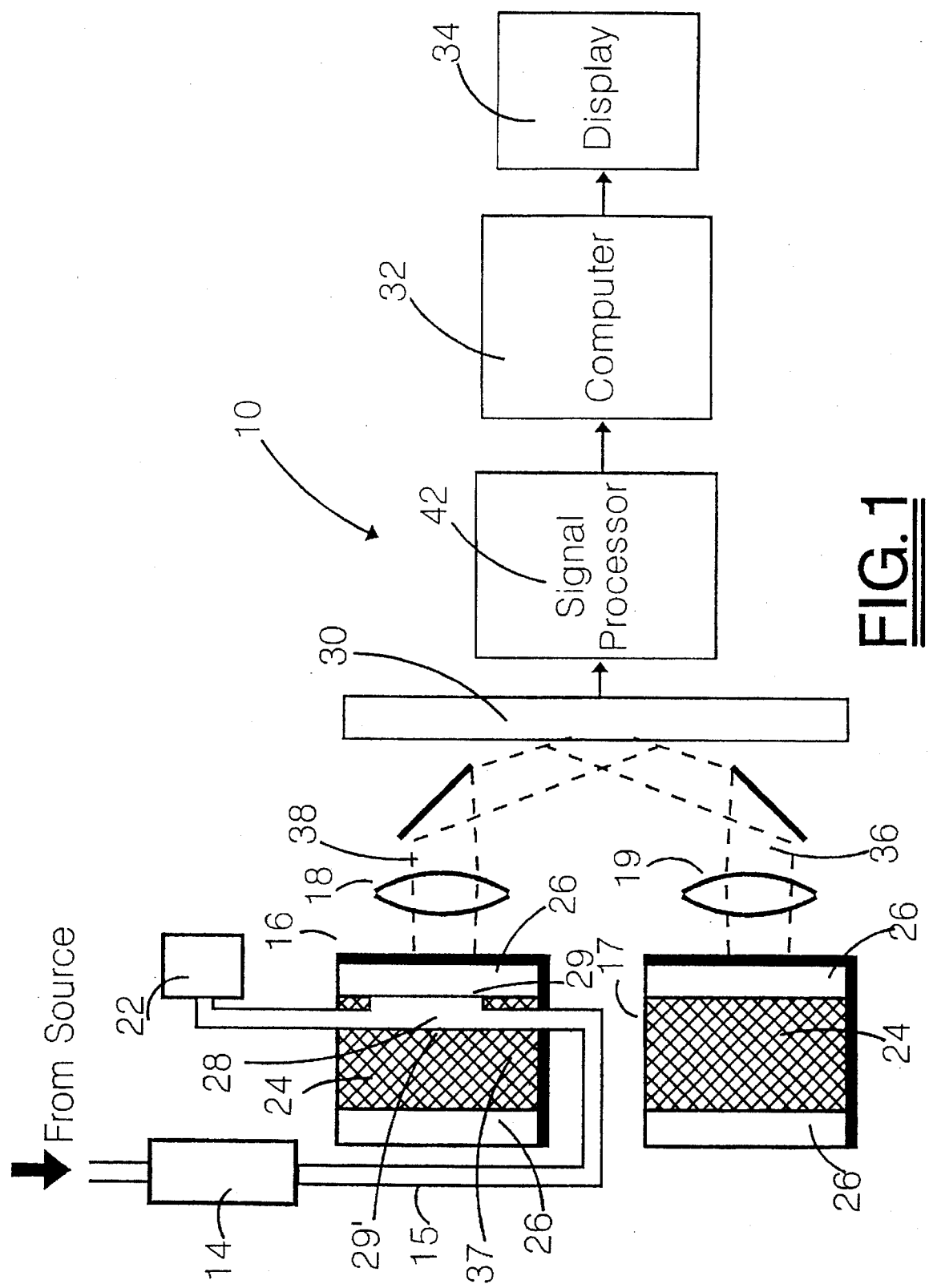
FIG. 1 is a semi-schematic diagram of an analytic system embodying the teachings of the present invention.

Turning now to the Drawings and to FIG. 1 thereof, there is shown an analytic system that embodies the teachings of the present invention. A fluid sample that includes a molecular species to be analyzed enters the system at the downward pointing arrow. This sample may have been subjected to any of the preanalytic steps described hereinabove or which are known to the art, as appropriate to the analysis of the molecular species. The sample enters separator 14, which can be embodied in several novel ways, as will be apparent from the discussion below. Separator 14 separates the molecular species of interest from other molecular species, either in a crude fashion, in which case undesired species will continue to associate with the molecular species of interest, or in a refined manner, in which case only the species of interest exits the separator 14. The effluent of the separator 14 is conveyed via a tube or channel 15 through a laser 16 containing a sample chamber 28. The flow of the molecular species through the sample chamber results in a frequency shift of the laser's output that can be observed. After leaving the chamber, the effluent is conducted to a sink 22 for further processing or disposal as may be desired.

To achieve optimum sensitivity using this technique, as well as to permit integration of the molecular detector in a planar geometry, it is desirable that the laser 16 be of the microchip type described in Mooradian, U.S. Pat. No. 4,860,304, which is incorporated herein by reference. This laser consists of a thin slab of optically pumped laser material which is closely coupled to a highly multimode diode laser which serves as the pump source. By providing reflective optical coatings 26, directly on the laser material 24, and/or closely coupled optical elements, single frequency operation can be obtained.

The frequency of operation, $v$, of the laser 16 operating in the fundamental transverse mode will be $$n\frac{c}{2L} = v$$

where L is the cavity length and n is an integer. In the case of a single frequency microchip YAG laser operating at 1.06 μm, then a change of one order number must roughly equal the operating bandwidth of 200 Ghz (for YAG). Thus, the maximum permissible cavity length will be 0.075 cm. Now within the microchip laser 16 we introduce a thin sample chamber 28 which could be on the order of 50 microns. This might be formed by means of a thin spacer between one of the cavity mirrors and the laser crystal, for example. To calculate the frequency shift associated with a small change in cavity length, we use $$dv = -n\frac{c}{2L^2} dL$$

In the case of a representative protein molecule, the deposited layer might be on the order of 150 Angstroms. For a cavity length change of 150 Angstroms in air, $$dL = 1.5 \times 10^{-6} \text{ cm}$$

and the frequency shift is 6.0 Ghz. If the frequency shift is created in the context of an aqueous cell environment, then the frequency shift would be reduced to a typical value of 0.5–1.0 Ghz or thereabouts, depending on the specific indices of refraction of the molecular layer and the solvent.

A sample chamber could be similarly added between the lasing medium and the reflector of a helium-neon single frequency laser, or a single frequency dye laser to produce a frequency shift of the output when a molecular species enters the sample chamber.

Measurement of this frequency shift is preferably accomplished using a second microchip laser 17 as a reference and combining the outputs, shown representatively as overlapping beams 36, 38, from the two lasers on a conventional photodetector 30 via optics 18, 19. The output of the photodetector 30 is a signal representative of the difference frequency of the two lasers. This signal is conditioned by signal processing electronics 42. By making the reference laser a tunable laser, this difference frequency may be selected to have a convenient value. As the sample is introduced into the test laser, the shift in the difference frequency output by the signal processor 42 is monitored by a computer 32 or similar analyzer as a function of time, leading to the measurement of the molecular concentration.

Light emitted by the microchip lasers 16, 17 is of a single frequency in each case at a given time, so that the optical electric fields from the two lasers may be written as $E_1 \cos(\omega_1 t)$ and $E_2 \cos(\omega_2 t)$. In a well known and conventional analysis the electromagnetic field for an optical beam is optimally represented via the so-called "analytic signal", $V(x, t)$, where x is a generalized spatial coordinate and t is a temporal coordinate, and where $V(x,t)$ is a mathematically complex function having real and imaginary parts. L. Mendel and E. Wolf, *Coherence Properties of Optical Fields*, Rev. Mod. Phys. 37:231 (1965). The real, measured electric field for a particular optical beam is obtained from $$E(x, t) = 2 \operatorname{Re}[V(x, t)].$$

The instantaneous intensity, $I(x, t)$, of an optical disturbance is, in this representation, given by $$I(x, t) = V^*(x, t)V(x, t),$$

When two beams from independent lasers are combined on the surface of a photodetector in a coincident and essentially parallel manner, then the optical intensity on the surface of the photodetector is represented by the total analytic signal $$\begin{aligned} I(x,t) &= V^*(x,t)V(x,t) \\ &= [V_1^*(x,t) + V_2^*(x,t)][V_1(x,t) + V_2(x,t)] \\ &= I_1(t) + I_2(2) + 2\sqrt{I_1(t)} \cdot \sqrt{I_2(t)} \cos[(\omega_2 - \omega_1)t] \end{aligned}$$

The two instantaneous intensity terms $I_1(t)$ and $I_2(t)$ are optical frequency terms which produce a DC signal in the photodetector output current. The remaining term accounts for a heterodyne electrical current signal in the photodetector output at the beat frequency between the two input beams. Note that in this summary discussion there is assumed complete, parallel, spatial overlap of the two independent laser beams on the photodetector in order to eliminate the spatial coordinate from the above analysis. If these conditions are not strictly met, a reduction beat frequency signal amplitude will occur in accordance with the above summarized, well understood principles. Referring again to FIG. 1, the preferred embodiment of our invention requires a spatial overlap of the two laser beams 36, 38 onto the photodetector 30.

In the case of microchip lasers, this beat, or difference frequency is at or below the microwave radiofrequency region. Optical heterodyne detectors are known in the art, and are described, for example in Bessho, U.S. Pat. No. 4,912,530, incorporated herein by reference. The heterodyne detector described therein can be modified by those skilled in the art to detect the beat frequency produced by lasers 16, 17.

In the preferred embodiment of this invention the reference laser 17 is proximate the sample laser 16 so that local environmental conditions influencing the operating frequency of the sample laser 16 similarly affect the reference laser 17. This reduces variation in the measured difference frequency of operation of the two lasers 16, 17 when organic molecular samples are introduced into the sample laser chamber 28. The observed frequency difference arises from the conditions of the sample environment alone. Because the pump light for the sample and reference lasers is conventionally introduced longitudinally via fiberoptic means (not shown), and because these pump means are of a similar transverse dimensional order to the microchip output laser beam, the laser excitation kinetics should be sufficiently similar for the sample and reference lasers to ensure that a stable frequency difference between the two laser beams exists prior to introduction of the organic sample into the sample chamber 28.

The sample chamber 28 is configured in either of two ways. For measurement of molecular concentration, an organic molecule specific affinity coating is placed on one, or optionally on both interior sample chamber surfaces 29, 29'. When a solution containing the target molecule is introduced into the sample chamber 28 a monolayer of the organic molecule is then deposited onto the coated surface or surfaces, effectively changing the cavity dimensions. This causes a shift in the frequency of the laser. During the course of deposition of the molecule onto the surface(s), the effective optical density of the layer builds up gradually; and the frequency of the laser thereby changes continuously. The time history of the change in the laser frequency is related to the concentration of the target molecule in solution.

To facilitate either mode of molecular detection described above, the microchip laser construction should be modified to permit a channel or groove to be fabricated into either the laser material, or into a cover plate which is attached to the laser material, and which carries one of the reflective coatings for the laser cavity. In the event that a specific affinity coating is to be applied, this coating might be applied to either the laser material surface, or to the cover plate surface, or to both. Since the transverse spatial extent of the oscillating mode in a microchip laser is on the order of 100 µm, the channel serving as the sample chamber should be of a similar width. A typical channel depth would be in the range of 10–100 µm, although specific molecular measuring requirements might dictate values outside this range.

The assembly of the cover plate to the laser medium is accomplished by known methods. The method of field assisted thermal bonding as described in Pomerantz, U.S. Pat. No. 3,397,278, incorporated herein by reference is suitable.

This arrangement will provide a sample region which is approximately 100 µm in diameter. In instances where, using molecular affinity coatings, a smaller sample surface area may be required, the microchip laser cavity may be modified according to the following prescription. On the surface of the laser medium facing the cover plate, a binary optic lens is fabricated such that it will focus close to or very slightly behind the cavity reflecting surface of the cover plate. The binary optic lens may be fabricated using conventional lithographic procedures. Also, using conventional lithographic procedures to mask the surface of the cover plate, a highly restricted area upon which to deposit the molecular affinity coating is created while the entire cross section of the laser field is accessed. This area could be as small as a few microns in diameter.

Referring now to FIGS. 2–4, alternate preferred embodiments of the sample laser 16 will now be described. In each case like components have reference numerals advanced by a multiple of 100.

In FIG. 2 a sample laser 216 has laser mirrors 226, 227 and a laser crystal 224 therebetween. A sample chamber 228, shown in cross section, is formed in the laser mirror 228 and is bounded by a cover plate 230. Pump light, exemplified by the left arrow in FIG. 2, enters the laser from the left, is lased therein, and a coherent light beam exits through the sample chamber 228 and the cover plate 230 to form the output beam, which is indicated by the right arrow. This embodiment is convenient to manufacture because different ligands can be applied to the portion of the cover plate that bounds the sample chamber 228, and different cover plates can be bonded to a common laser structure 226, 224, 228 for different applications.

In FIG. 3 an alternate embodiment of the sample laser 316 is shown. Its general construction is similar to the embodiment of FIG. 2, except that the sample chamber 328 is formed entirely within the laser crystal material 324. This embodiment is convenient when it is not intended to coat the wall of the sample chamber with a ligand.

Yet another embodiment of the sample laser is shown in FIG. 4. This embodiment has the same general construction as the embodiment of FIG. 2. A sample chamber 428 is formed in the laser mirror 428, and is bounded by a portion of a cover plate 430. However now a microlens 435 is positioned in the laser crystal 424 proximate the sample chamber 435. The microlens is a binary optic lens of the type discussed hereinabove. It converges the laser output beam 432 onto a small region 434 of the wall of the sample chamber 428. Reduction of the field of view allows for a smaller amount of ligand to be deposited on the wall of the sample chamber. This can significantly reduce expense in cases where the molecular affinity coating is expensive, or technically difficult to reliably apply.

Many kinds of surface chemistries are available in the art to provide specific molecular recognition ligands on the surfaces 29, 29' for any conceivable molecule of interest. Both nucleic acids and proteins can be bound or even synthesized on the solid support system and act as specific detection molecules. Much work has been directed towards the development of solid support surface linkage groups in *affinity chromatographic* applications. This work has direct application in the present detection system. In affinity chromatography, a binding ligand is immobilized on a solid support via a spacer group. The solid support is often agarose, crosslinked dextrans, or controlled pore glasses. A typical spacer is aminocarboxy-hexane. The bound ligand may be a hormone receptor, an antibody, or the substrate for an enzyme.

Peptides can be synthesized on a solid support. A classic example of protein synthesis on a solid support is the Merrifeld solid state synthetic method (B. Merrifeld, *Science* 232, 341 (1986)). This technique combines amino and carboxyl protecting groups with peptide coupling reagents. Synthesis is carried out on a polystyrene matrix. A reactive center is introduced into the polymer support by chloromethylation. The benzyl chloride linkage is easily replaced by the carboxyl function of the first amino acid in the synthetic chain. Random peptides can be built up as required. The solid state electrophoresis system disclosed here is amenable to parallel synthesis of a combinatorially large array of peptides if required.

Light directed solid state synthesis can also be used to build up a combinatorially large number of peptides on planar substrates as described by Fodor, et al, *Science* 251, 767 (1991) of the Affymax Research Institute. These investigators use the amino group at the ends of linkers attached to a glass substrate to initiate photoactivated synthesis. The amino groups are derivatized with nitroveratryloxycarbonyl, a photoremovable protecting group. Fodor, et al also describe light directed nucleic acid synthesis on a glass substrate. Affymax Corporation is the first group to develop planar systems for the synthesis of a combinatorially large number of dissimilar chains of peptides and nucleic acids. They use a novel, lithographically based, photon driven combinatorial approach using the chemistry referenced above. The system relies upon the generation of a programmable mask that can define regions of photochemical driven chain elongation on a substrate. By repetitive application of various masks, a large number of protein or nucleic acid chains can be defined for drug testing or clinical use.

Other organic molecules can be synthesized on solid substrates. Monoacetates of symmetrical diols (Fyes and Leznoff, *Can. J. Chem.* 54, 935 (1976)) and insect sex attractants (Leznoff and Fyles, *Can. J. Chem.* 55, 1143 (1977)) have been produced using polymer supported organic synthesis. However, the application of solid state supported organic chemistry to develop a combinatorial array of ligands has not yet been accomplished for drug discovery (as pointed out by Moos, et al, *Annual Reports in Medicinal Chemistry* 28, 315 (1993)) and certainly not for development of specific organic assay ligands.

A simplified version of a detector system is now explained with reference to FIGS. 1–4. This can be used to detect the presence of a molecular species in an electrophoretic separation system, which is inserted into the arrangement of FIG. 1 as separator 14. In this case a sample laser having an uncoated sample chamber, such as the laser shown in FIG. 3, is used as laser 16. It is configured to be a portion of the electrophoretic separation flow path by an appropriate disposition of the electrophoretic electrodes (not shown). As molecules collect into bands, the passage of a band through the sample chamber will cause a frequency shift due to the increased index of refraction of the molecular aggregate compared to that of the background solution. This kind of detection requires no labelling of the molecules, and, in the preferred embodiment described above, uses infrared radiation which avoids possible dissociation of molecular bonds on absorption. Using the microchip laser example above, if the sample cell has a thickness of 50 µm and a minimum detectable frequency shift of 10 MHz is assumed, then this detector will be sensitive to an index of refraction change of less than 1 ppm. This means that extremely faint molecular bands may be detected. The deposition time depends on the concentration of the substance being detected, and the frequency shift once the binding sites have been saturated is a function of molecular size of the substance. The signal developed by the detector can be used in kinetic analysis, wherein different binding affinities of related molecular species are an indicator of a species, or the signal can simply provide an qualitative indicator that a species of interest has passed through the detector. Kinetic analysis is well known to the art, and will therefore not be further discussed herein.

We now disclose a complete system for separation, sequencing and assay of cellular DNA to illustrate the various aspects of operation of the invention, and which can be understood with reference to general system of FIG. 1. In standard DNA gel electrophoresis, there are considered to be three DNA size and behavior groups in separation. These groups are identified by strand lengths less than 500–1000 base pairs (bp), $10^3$–$10^6$ bp, and lengths greater than $10^6$ bp. By way of reference, a mammalian chromosome is close to $2 \times 10^8$ bp in length.

DNA fragments with a length below about 1000 bp move in gels in a relatively standard and well understood way. The DNA fragments display a logarithmically monotonically enhanced mobility as a function of decreasing molecular weight. The gel acts as a standard molecular sieve. The larger the molecule, the more sieve collisions, and the slower the molecular movement in the applied field.

Between $10^3$ and $10^6$ bp, DNA electrophoretic motion changes. In a standard one directional field the DNA fragments lose their ability to separate by molecular weight. This is thought to be related to loss of complete chain rotational freedom and complete strand elongation in the direction of the applied field. If the strands orient in the field direction they will all display a similar projected cross section to the gel and hence loose the property of size dependent sieving. However, as shown by Cantor, et al (1988), by application of a crossed electric field to the separation region, separation of chains by molecular weight can be recovered. The crossed field is thought to cause the molecules to orient at an angle to the separation axis, enhance molecular cross sections, and hence recover size dependent sieving. In addition, gel simulations and experiments support the idea of a reptation motion (coiling and uncoiling) of DNA strands greater than $10^3$ bp in length. In reptation the long strands wrap around the gel polymeric chains and are pulled free by the applied field. The longer the strand, the more reptation the chain will undergo. During the coiling phase of the motion, the gel will provide better sieving action than during the straight motion of the chain in the elongated state.

DNA chains longer than $10^6$ bp do not migrate in gel electrophoretic systems. Viovy et al. have suggested that the long DNA chains wrap around the polymer fibers and become trapped or knotted, restricting motion. On the other hand, Vurlatsky and Deutch have suggested that the long chains display significant static molecular frictional forces during extended contact with polymer gels. Large contact areas orthogonal to the direction of separation are enough to arrest chain motion in the gel. The lithographically fabricated sieves described above overcome this problem and will permit separations up to $10^8$ bp chains.

Figure 5:
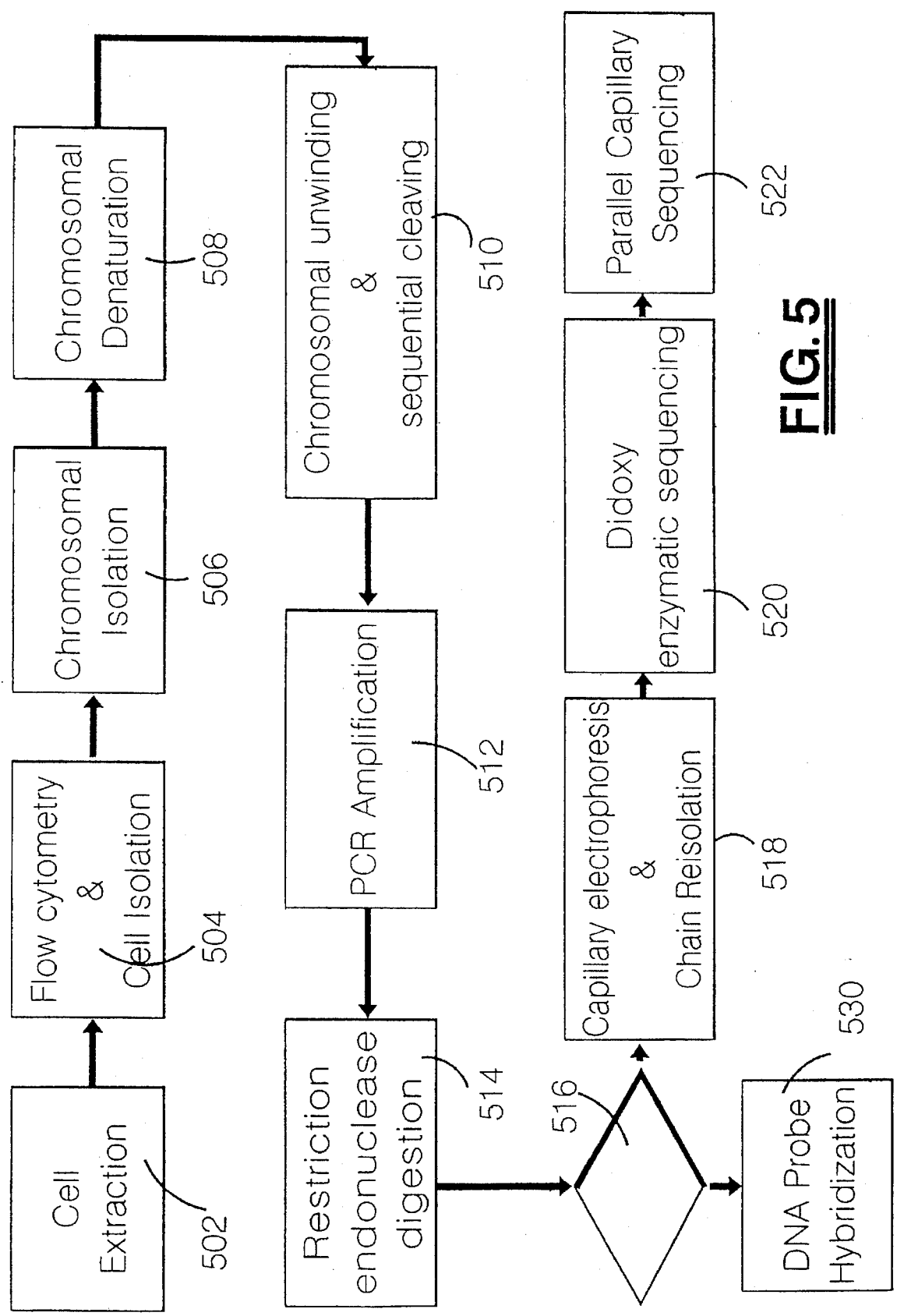
FIG. 5 is a flow diagram illustrating a method of chromosomal analysis that can be practiced according to the invention.

A complete separation is explained with reference to FIG. 5 and begins with cell isolation at step 502. Cells are first sorted based upon desired characteristics in a cell sorting Flow Cytometer at step 504. Cell sorting can be based upon a myriad of cytological characteristics and specific fluorescent stains. In this discussion we assume the cell (or cells) of interest contain metaphase chromosomes.

Figure 6:
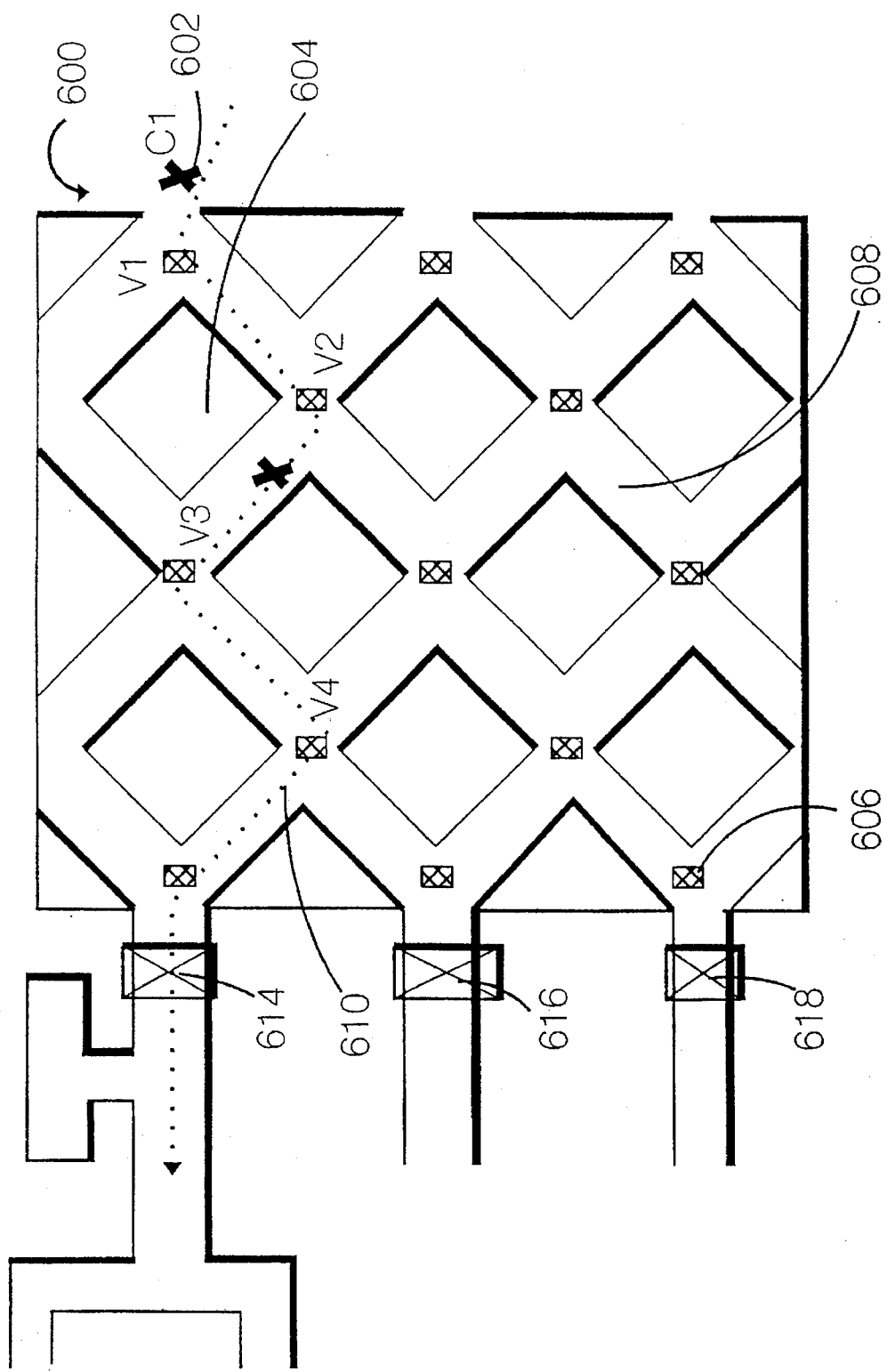
FIG. 6 is a partially schematic plan view of a two-dimensional lithographically formed nanostructure suitable for separation of chromosomes with the cover plate removed.
Figure 7:
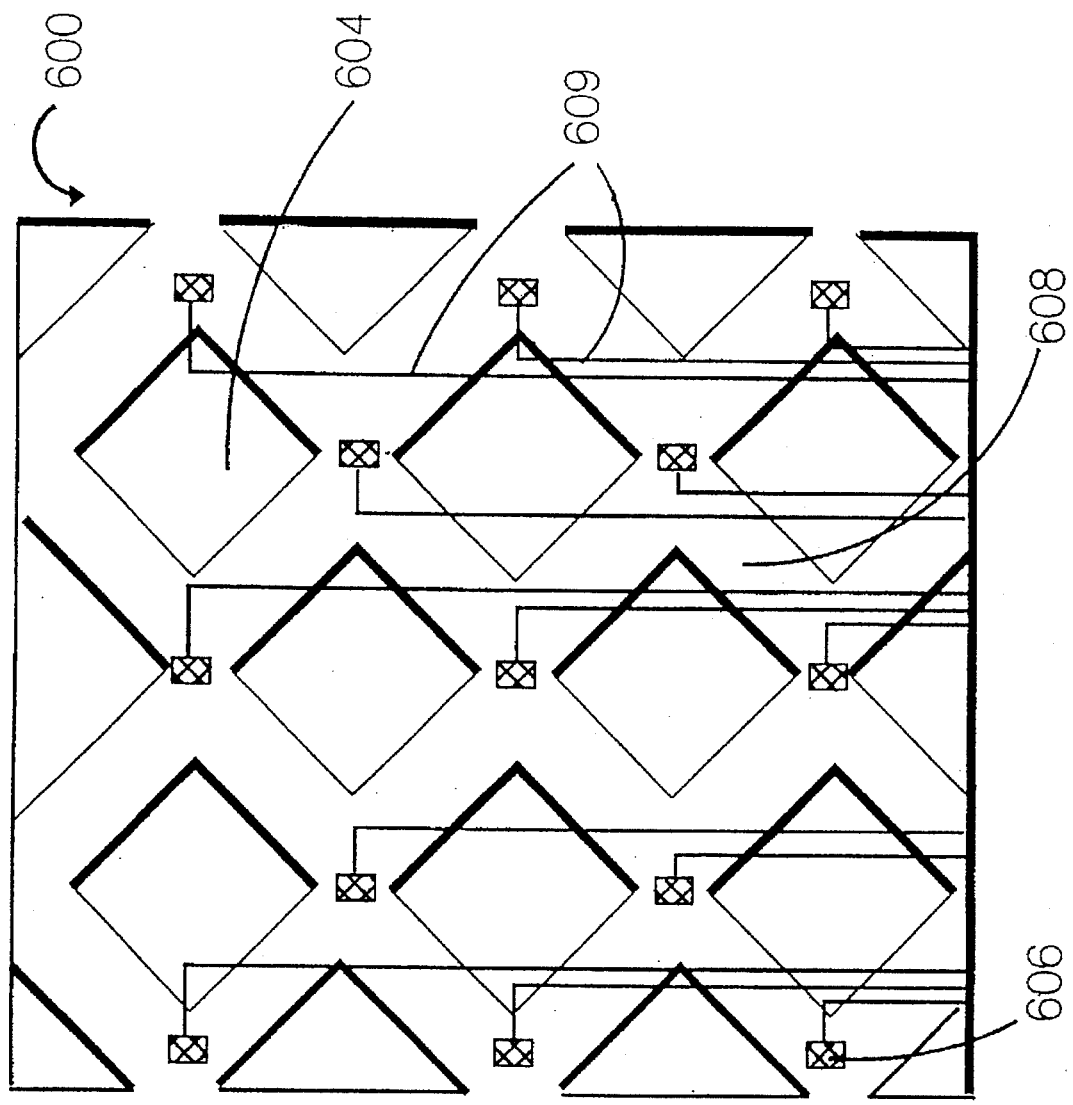
FIG. 7 is a plan view similar to FIG. 6 with detail added.
Figure 8:
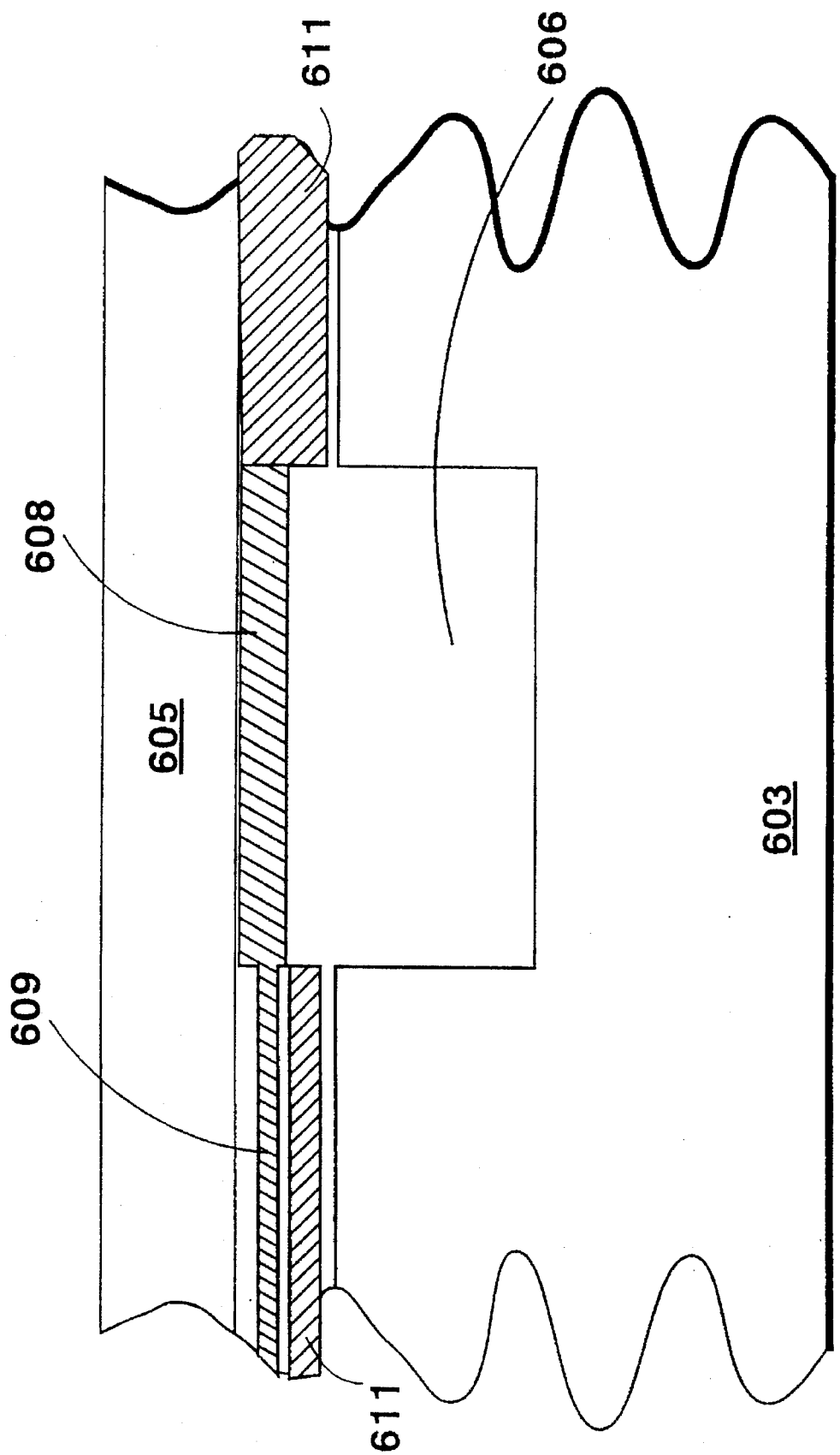
FIG. 8 is a partial sectional view of a nanostructure similar to the nanostructure shown in FIG. 6 with the cover plate in place.

After cells of interest are sorted, individual chromosomes are isolated at step 506 by standard means and visualized in a high power microscope. The chromosomes may be labelled in a variety of ways to enable their identification. The chromosomes are then introduced into a small channel on a planar, two dimensional substrate. FIGS. 6–8 show a two-dimensional matrix 600 of electroosmotic channels that can accomplish this task. Chromosomes 602 are applied to the right side of matrix 600, configured as a diamond array, via electroosmotic flow, as indicated by the three leftward directed arrows. The chromosomes 602 enter the diamond array at random. The chromosomes 602 can be fluorescent labelled for identification prior to their entry into the matrix 600. Banding patterns or color can also be used to distinguish each chromosome.

The diamond array of obstacles is defined lithographically. The diamonds 604 can be several hundred microns on a side. Preferably they are 200–300 microns on a side, and the channels 606 through which the chromosomes flow are preferably 10–50 microns wide. Electrical conducting pads 608 are placed at intersections of the channels 606, which are also abutment points of the vertices of the diamonds 604. These pads 608 are defined lithographically in a quartz substrate 603 prior to the placement of the diamonds 604. The pads have leads 609 which are plated, and then covered with a $SiO_2$ layer 611, which is applied by chemical vapor deposition techniques, to allow only the pads 608 to be exposed to the electroosmotic solution in the channels 606. The leads are connected to a suitable electrical voltage source (not shown). A quartz cover plate 605 is disposed above the leads 609, pads 608 and the separation channel 606.

After visual identification of a particular chromosome, an electroosmotic flow path is defined by adjusting the potentials of the appropriate electrodes. For example a particular chromosome C1 is located at pad V1. A potential drop is defined along path 610 (V1-V2-V3-V4) leading into channel 1. Channels 1–3 are guarded by microvalves 614–618 respectively. The microvalves are well known in the art, and are available from IC Sensors, Milpetas, Calif. Only microvalve 614 is allowed to be open. All other valves are closed. The microvalves are actuated electrically via wires leading to a control device (now shown).

Potential throughout the path 610 is varied to ensure chromosome movement in a desired direction. Initially all pads to the left of C1 are held at a high potential. A potential drop is developed from V1 to V2. V3 is held at a lower potential than V2, but the potential gradient from V1 to V2 is larger than from V1 to V3, which ensures that there is significant fluid flow in the channel therebetween. This arrangement allows a movement of chromosome C1 from V1 to V2. After chromosome C1 reaches V2, the potential drop from V2 to V3 is increased, to insure a desired flow rate. Other chromosomes 602 will be located at a distance from chromosome C1, and will not move significantly until their local pads are switched on. It has been found that electrical gradients between 1,000 and 10,000 volts/meter are suitable.

Figure 9:
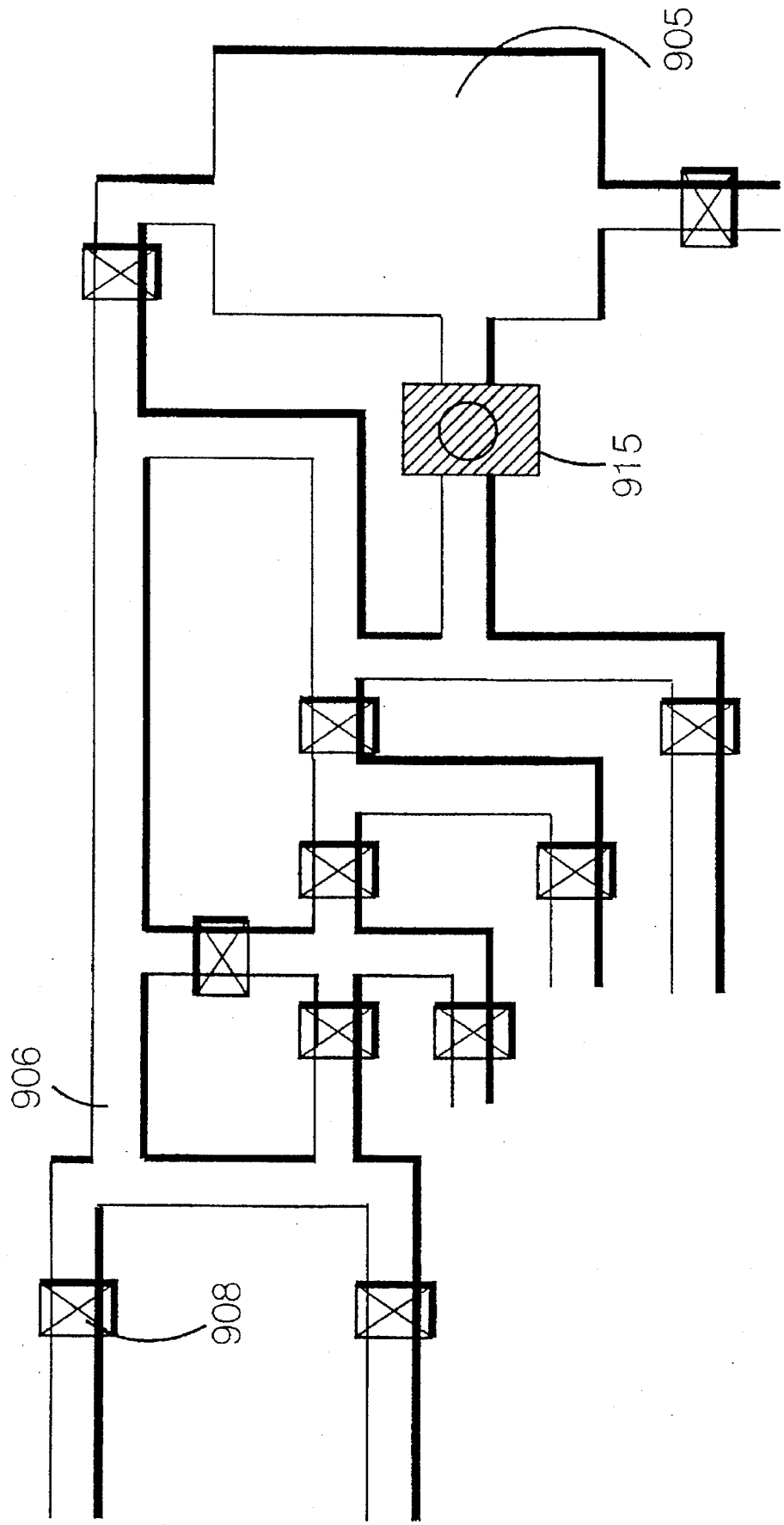
FIG. 9 is a diagrammatic view of another lithographically formed device on a two-dimensional substrate suitable for the separation of chromosomes in accordance with the invention.

Another structure suitable for isolating chromosomes is shown in FIG. 9, and is configured as a binary boolean tree. The channels 906 in this structure can be defined lithographically in a planar structure having a construction similar to that shown in FIGS. 7–8, except now the leads and electrical pads are not required. Instead a plurality of microvalves are strategically placed so as to permit a chromosome flowing along the network of channels 906 to follow one of two possible courses at each branch point. Five levels of binary branching points allow 32 different paths for the isolation of chromosomes. Since the human cell nucleus contains 23 distinct chromosome pairs, five branches are adequate for a full separation. The network is referred to as a boolean tree, because isolation microvalves 908 are incorporated at suitable branch points to open and close pathways. It is also possible to incorporate electrical potential switching functions, constructed as described with reference to FIGS. 7–8, in order to direct the flow of chromosomes through the channels under the influence of a suitable electrophoretic field.

The key to operation of the switching tree is to insure that chromosomes migrate out of a supply reservoir 905, or that during flow through the reservoir output channel the linear flow velocities of the chromosomes are sufficiently distinct to lead to a differential migration in the applied field. Since all chromosomes have distinct sizes, this condition is likely to obtain. As the chromosomes migrate through an optical imaging station 915, they are identified, and it is decided which sequence of microvalves are thrown in order to direct the chromosome down the correct separation lane.

Figure 10C:
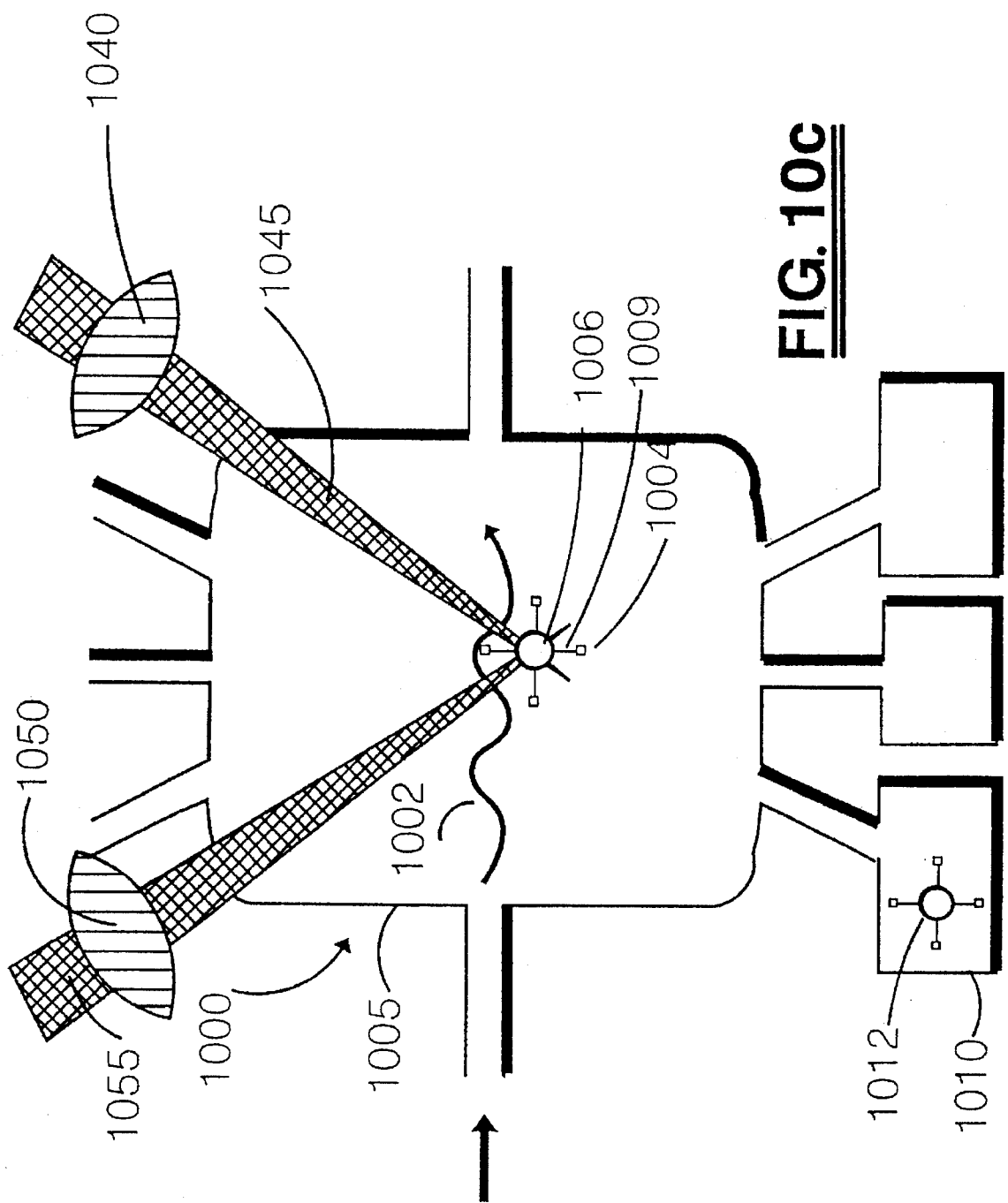

Yet another approach to chromosome isolation can be understood with reference to FIGS. 10a–10c, wherein discrete restriction enzyme slicing of the chromosomal DNA is performed at intervals of 100–1000 kbp. To accomplish the slicing, it is necessary to quickly expose and shield the migrating DNA chains to and from the restriction enzymes. There are several methods that can be applied to this problem. There are basically two modes of enzyme presentation: 1) pulsed bound enzyme presentation; and 2) pulsed free enzyme presentation. Embodiments of the presentation chambers are described in both cases.

1) Pulsed Bound Restriction Enzyme Presentation

The major issue in pulsed presentation of the enzyme to the electrophoretically migrating DNA chain is enzyme localization. It is important to cleave the chains in a discrete area of the chain. Furthermore it is important that the enzyme does not diffuse along the chain to cause scission at multiple random places. Localized presentation and limited diffusion are best accomplished if the restriction enzymes are bound to solid supports that can be withdrawn from the DNA migration path during chain electrophoresis. Referring first to FIG. 10a, this can be accomplished with restriction enzymes 1004 bound to glass beads 1006 through standard linkage groups 1009. In FIG. 10a an isolation system, referenced generally at 1000 includes a pulsing chamber 1005 through which flows a chromosome 1002 in the general direction indicated by the solid arrow at the left of the figure. A magnetic field generator 1020, under the programmed control of a microprocessor 1030 produces a pulsed magnetic field whose polarity periodically reverses, in which representative flux lines are indicated by the three dotted arrows pointing generally upward and to the right. The beads 1006 contain magnetic material, and the beads traverse the chamber in response to the pulsed magnetic field, and they can be brought from a reservoir 1010, into contact with a chromosome 1002 for a controlled period of time, after which they are returned to the position of bead 1012 in reservoir 1010. This method has the advantage that the beads can very quickly traverse the chamber 1005.

In FIG. 10b there is shown an arrangement for controlling the flow of the glass beads 1006 by electroosmotic flow. The construction of the pulsed chamber 1005 is the same as in the embodiment of FIG. 10a, except now a suitable electric field, indicated by the "+" and "−" symbols above and below the chamber, is applied, causing the beads to migrate into a desired position. This method is simple, but has the disadvantage of affecting the flow of the chromosome 1002. This may complicate the control of the chromosome during the cleavage process.

FIG. 10c shows yet another technique for controlling the migration of glass beads utilizing optical tweezers. Optical tweezers advantageously employ dipole forces that arise from the coherent interaction of small particles with laser light, as is described in greater detail in Chu, *Science* 253:861, 23 Aug. 1991. A chamber 1005 has the same construction as the embodiment of FIG. 10a. Glass beads 1006 about 1 micron in diameter are trapped by two overlapping laser beams 1045, 1055, which are focused on the beads by suitable optics 1040, 1050 respectively. The beams are manipulated to microposition the beads at a desired location of the chromosome 1002. Although only one optical tweezer is shown in FIG. 10c for clarity, multiple optical tweezers can be used for beads that bind different restriction enzymes. Class II restriction enzymes are appropriate in this application.

2) Pulsed Free Restriction Enzyme Presentation

It is also possible to expose the chromosomes in a cleavage chamber to enzymes electroosmotically flowing therein in an unbound state. A conventional electrical power supply is used to generate a cyclically reversing electric field for electroosmotic flow of the enzyme into and out of contact with the DNA. In an alternate embodiment, which is explained with reference to FIG. 10d, independent flow control of the enzymes 1004 and the chromosome 1002 is provided by control of sieve size, taking advantage of the fact that restriction enzymes are smaller than chromosomes or other DNA fragments to be analyzed. Lithographically created molecular sieves 1060 are positioned between the reservoir 1010 and the main chamber of the pulsing chamber 1005. The nanostructures of the molecular sieve are suitably dimensioned so that the enzymes 1004 can flow therethrough under the influence of an electroosmotic field, indicated by the "+" and "−" symbols in FIG. 10d. The chromosome 1002, or fragments thereof, are too large to pass through the sieve. By appropriately moving the enzymes 1004 in and out of the reservoir, it is possible to independently control the movement of the enzymes 1004 and the chromosome 1002 in and out of the pulsing chamber 1005.

Figure 11:
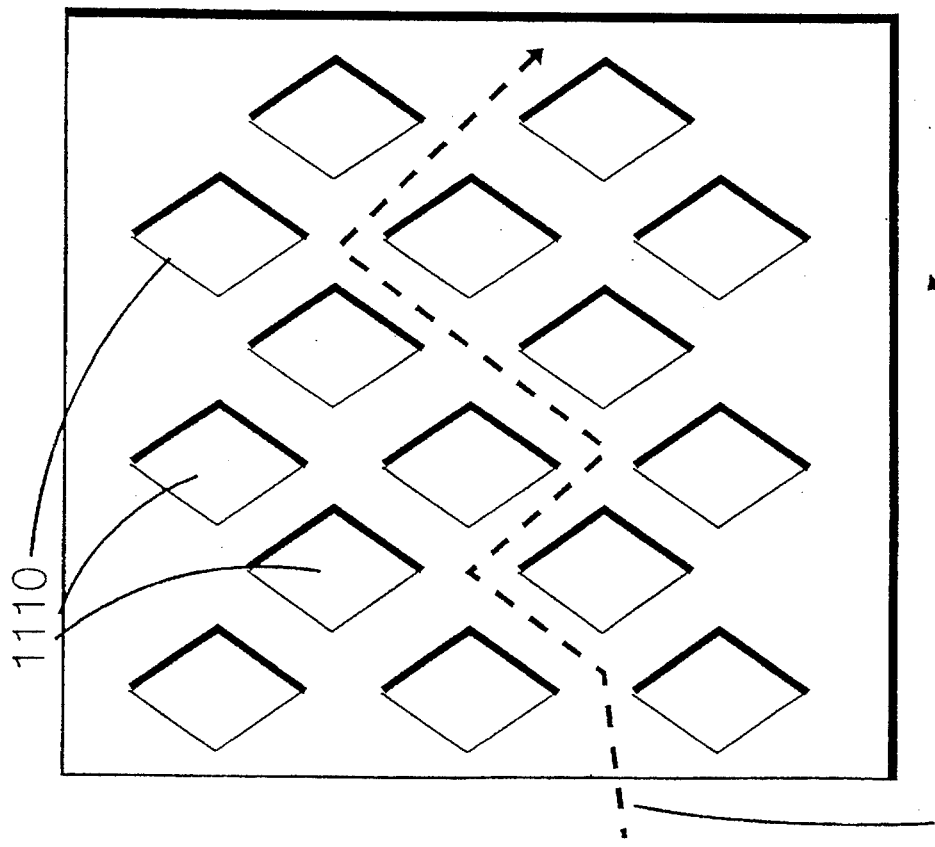
FIG. 11 is a plan view of a nanostructural molecular sieve formed on a two dimensional substrate for separation of molecular species with the cover plate removed.

Turning now to FIG. 11 a molecular sieve 1100 suitable for use in the embodiment of FIG. 10d is constructed of an array of raised diamond-shaped posts 1100, lithographically formed in a substrate and spaced apart to define a series of channels therebetween. A sufficiently small molecule can flow through the array in a path, such as path 1115. A cover plate (not shown) is placed over the array to form a roof, similar to the arrangement shown in FIG. 6, except that electrodes and leads are not required. For large fragment DNA analysis the posts 1110 are about 0.5 microns on a side, and the channels defined by sides of two adjacent diamonds 1110 are 0.5 microns in width. In either case the sieve is dimensioned to admit the restriction enzymes, but not the DNA fragment or chromosome. The posts 1100 can also be constructed in large numbers of columns according to a spatial gradient, in which case it can function as a molecular sieve in which the transit time of molecules varies according to their molecular weight, as well as their spatial configurations.

Figure 12:
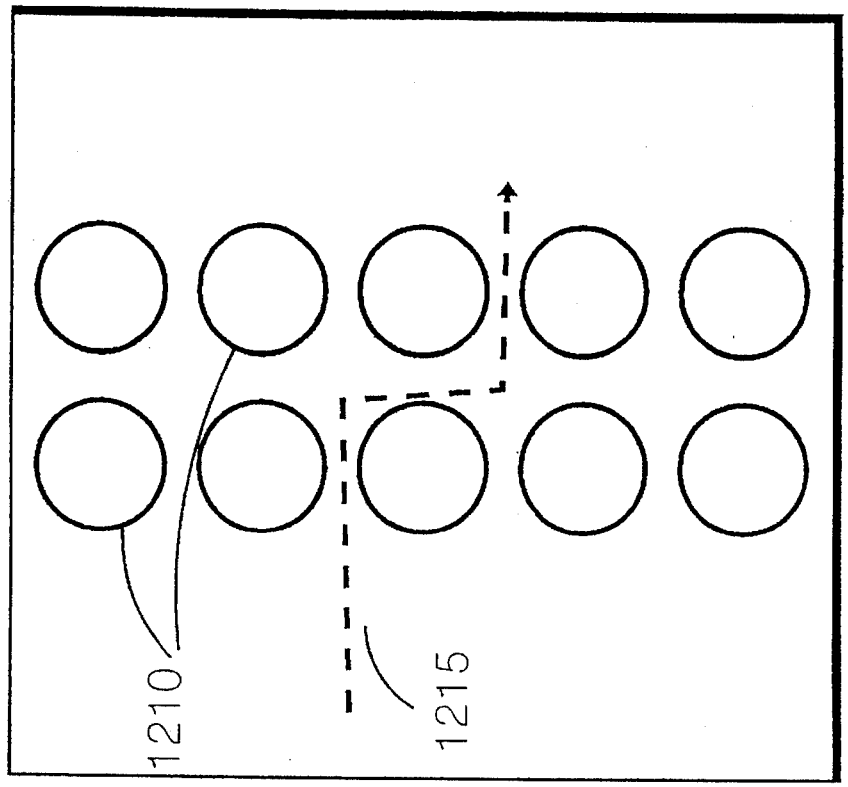
FIG. 12 is a plan view of an alternate embodiment of a nanostructural molecular sieve formed on a two dimensional substrate for separation of molecular species with the cover plate removed.

In FIG. 11, and in FIG. 12 only a few nanostructures are shown for clarity, it being understood that in practice a much larger number of nanostructures are employed as necessary to achieve a desired sieving action. We can calculate the number of lithographically defined posts required in a separation lane. In gel electrophoresis separation is a stochastic process; the molecules moving with the field collide at random with the gel matrix. For molecules to segregate into defined zones there must be many collisions such that on average, all molecules with the same molecular weight experience the same number of collisions within some range defined by a standard deviation. If one wishes the standard deviation to be small (say less than 3% of the number of collisions) and all the zones to have enough separation time (or distance) to be resolved, then the total number of collisions must be on the order of n=100,000, where n is the number of collisions with the post matrix. If the collisional process is truly random then the standard deviation is $\sqrt{n}$ or approximately 300. In the solid state sieve the open cross sectional area for fluid and particle flow should be between 2 and 50 times the area obstructed by posts. So, for example, if the post size is 0.1 μm in diameter, and the particles are 40–100 Angstroms in diameter (or effectively point particles), the mean free path between collisions would be in the range of 0.2–5.0 μm. If a separation distance for the lightest particle involves 100,000 collisions, with each collision separated on average by 3 μm, the approximate separation distance required would be 30 cm. The separation lane diameter would be about 30 microns. For an array pattern of uniform density in the direction of separation and the orthogonal direction, the number of posts in a single lane would be approximately one million.

FIG. 12 shows another embodiment of a molecular sieve suitable for separation of DNA fragments of $10^3$–$10^6$ base pairs. Two columns of posts 1210 are arrayed proximate one another such that the posts are all spaced 0.1–0.2 microns apart from one another to define passages therebetween. The posts 1210 are each 0.1–0.2 microns in diameter. A cover plate (not shown) roofs the sieve, and the operation is as describe with reference to the previous embodiment. A restriction enzyme can pass through the sieve, following a path 1215 for example. The DNA fragment is too large to pass through.

Referring again to FIGS. 1 and 5, in FIG. 1, separation of an organic molecular species in separator 14, wherein the species is a chromosome, can be realized by performing steps 502–506 with the embodiments described hereinabove.

After isolation, at step 508 chromosomes are collected in a microreaction chamber on the two dimensional substrate. The chamber's construction can be similar to that of the pulse chamber of FIG. 10a, and will therefore not be repeated for brevity. Here chromosomes are denatured by known methods. DNA is unwound from histone and non-histone type proteins. Isolated DNA at this stage can be many millimeters long, and composed of up to $2\times10^8$ base pairs. Sequencing a structure this long is presently beyond the state of the art. In addition, long DNA strands are highly susceptible to breakage from mechanical shearing forces. The electrostatic flow system disclosed herein gently handles DNA and will facilitate directed motion of exceptionally long, unbroken chains. The longer the DNA molecule that can be handled in a defined way, the faster and more simply it can be sequenced. Furthermore, if sequences can be assigned to specific chromosomal sections (parts of a physical gene map) the sequencing task is greatly simplified. Alternatively, if the goal is the specific hybridization of cellular DNA to certain DNA probe molecules in order to preselect certain sequences for further analysis, separation of long defined chain sections is again advantaged. We will first discuss total DNA sequencing.

The first step in large fragment isolation is chain straightening in an applied field at step 510. Long chromosomal fragments are oriented in an applied field. To aid in elongation in the field direction, chains will be directed through a lithographically fabricated lattice of micron sized structures. Small scale sieving is not attempted at this stage in order to minimize chain tangling and electrophoretic immobility.

At this point the migrating chains feed through microdigestion chambers, as have been previously described with reference to FIG. 10a–10d, and undergo pulsed exposure to restriction enzymes. These enzymes may be immobilized on microbeads to prevent diffusion along the electrophoretic axis. The DNA chain will be scissioned at approximately $10^6$ bp intervals. This process is used to slice an entire chromosome into sections.

The isolated fragments are now electrophoretically transported through channels approximately 20 μm wide and 1 μm deep filled with lithographically fabricated, diamond shaped, solid nanostructures with 0.1–0.2 μm spacings to maintain chain elongation. The construction of such an array has been described with reference to FIG. 11, and is not repeated for brevity. These channels may be used to switch or direct chains between multiple parallel Polymerase Chain Reaction (PCR) amplification stations at step 512. PCR amplification has been shown to be effective enough to allow direct DNA sequencing without the need for a separate growth and replication medium. At this stage a further restriction enzyme digestion step 514 may be required to reduce DNA lengths to $2–4\times10^4$ bp for PCR amplification with presently available techniques. Because the channel structures maintain DNA chain orientation, it should be possible to greatly extend the length of segments processed by PCR.

The amplified chains may then be transported through further nanostructure bearing channels to chambers for further digestion, separation, and sequencing. (indicated by the dotted feedback line 517 in FIG. 5). Alternatively, the chains may be used directly for DNA probe hybridization as discussed next.

After amplification (or, if multiple cells are used for DNA extraction, without amplification) DNA probe hybridization may be attempted at step 530 to immediately identify certain sequences. Alternatively, further restriction digestion at step 518 may be attempted prior to probe annealing. Additional separation can be done conventionally using enzyme synthesis at step 520. The method of Fodor et al, described above, can be used at this stage. Additional sequencing using parallel capillary sequencing or electrophoretic plates is conducted at step 522 by known means.

A novel embodiment of a probe system that can be used in conjunction with steps 518 and 530 is next described with reference to FIGS. 13 and 14. The system 1300 consists of DNA probes that are disposed in a linear array of probe chambers 1305. Single stranded DNA is introduced through port 1303 and electrophoresed over probe chambers 1305. After binding, denaturing reagents flow from reservoir 1302 through appropriately opened microvalves 1310. Chain melting is thus initiated. Bound molecules are eluted and transferred to a readout column 1325. The laser detection system 1320, the construction of which has been described above, is used to observe the presence and concentration of bound molecules. A representative output of the laser detector 1320 is shown in the graph at the right of FIG. 13, indicted generally by reference numeral 1340.

It is possible that site specific mutations are present in the bound DNA, or that several nearly identical sequences have bound to the probe. To address this issue the system can be structured for further digestion and reannealing to smaller probe molecules that are placed in probe chambers 1330. Complete sequence assurance is determined by further amplification and sequencing as may be desired. The rebinding step, or output of the eluate to a sink 1335 following detection by the laser detector 1320 can be selected by appropriately actuating microvalves 1312 and 1313.

The enzymatic chain termination approach of Sanger to DNA sequencing is preferred here over the chemical cleavage approach of Maxam and Gilbert because of enhanced sensitivity and ease of terminal labeling. Today most gel sequencing systems can function up to about 300 bp units. It has been proposed that ultrathin gels (less than 0.1 mm thick) and capillary electrophoretic systems have the potential for single step sequencing of up to 1000 bp. The solid state sequencing sieve disclosed here incorporates aspects of both ultrathin gels and capillaries. Thicknesses can be down to 1 μm or less. The disclosed system should be able to sequence more than 1000 bp in one attempt.

The steps described with reference to FIG. 13 can be further understood as a time ordered sequence with reference to FIG. 14, wherein the DNA binding step 1405, the elution and concentration step 1410, the detection step 1420, and the rebinding assay 1430 occur sequentially.

The $10^5$ bp PCR fragments must therefore be cleaved into one kilobase lengths for final sequencing. As described above, cleavage may be performed in a defined sense using restriction enzymes. The resultant chains are then reelectrophoresed to separate identical chains prior to final sequencing. Over 100 parallel sequence systems can easily be placed upon a single 50 mm×25 mm section of a DNA sequence plate fabricated according to the prescription in this disclosure.

Readout of the final sequence information may be achieved by fluorescent detection of labeled terminal dideoxynucleotide analogs or by using labels having absorption bands which encompass the laser wavelength of the laser based detector disclosed herein.

Full genetic sequencing is a major undertaking. It is unlikely that a single plate can be developed to sequence an entire human genome in a single day. An optimum single plate may hold 100–1000 parallel final sequence channels for 1000 bp at a time. Thus we estimate that a single plate may sequence $10^6$ bp every 4–8 hours. A full genome sequence of $10^9$ bp may require 100 plates in operation for 1–20 days. A full scale system such as this could be built in a cabinet 2 m×2 m×5 m. However, 90% of the human genome is composed of non-coding sequences. Using a probe based approach, the coding sequences may be isolated prior to full sequencing. This substantially reduces the time and effort required for sequence determination. It is possible that a probe based sequencing system of 10 plates could determine the entire coding sequence of a human genome in a single day. Such a system will be of great benefit in the area of genetic testing.

Figure 15:
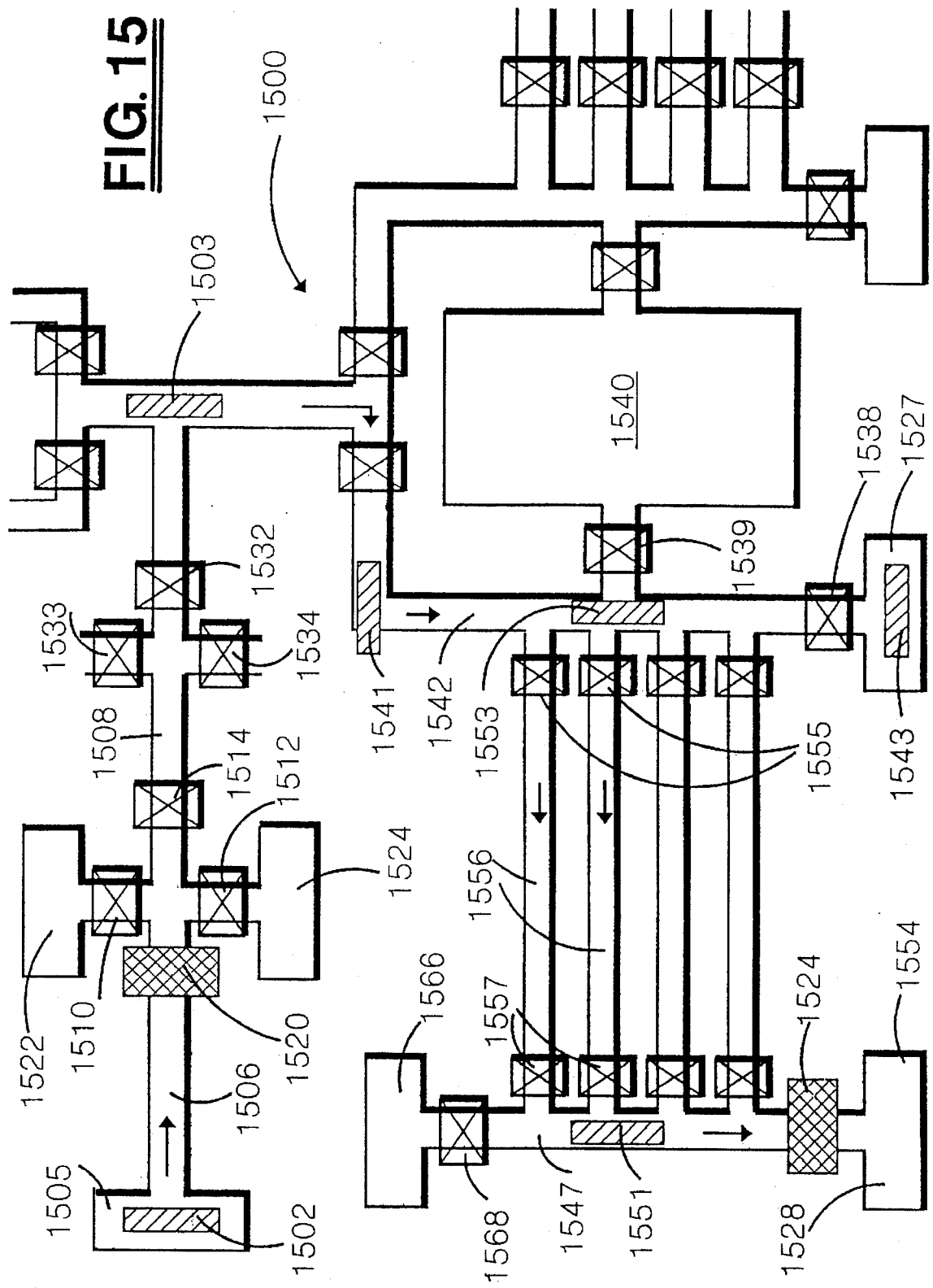
FIG. 15 is a schematic diagram of a multidimensional separation system that is fabricated on a two-dimensional substrate.

Referring now to FIG. 15, there is shown an alternate embodiment of the invention which is suitable for analyzing species of organic molecules that are separable by multidimensional electrophoresis and variants thereof. In a system 1500, all structures are configured on a lithographically defined planar substrate as described above. Molecules to be analyzed, which could be proteins, peptides, pharmacologically active substances of various types, or the like, are initially in reservoir 1505. An electrokinetic axis is established by electrodes 1502, 1503, and the molecules migrate under its influence along a first dimension in channel 1506 toward the rightmost electrode 1503. A first laser detector system 1520, which is of the type shown in FIG. 1, is disposed in the channel 1506 for detecting bands of molecules migrating therealong in a first dimension. The laser detector preferably is realized according to the embodiment of FIG. 3, as it is not generally required to coat the surfaces of the sample chamber with a ligand. After having passed through the laser detector system 1520, the molecules are guided into a selected one of sinks 1522, 1524, or along channel 1508 by appropriately controlling microvalves 1510, 1512, and 1514, and enabling suitable electric fields (not shown). The remainder of the discussion of this embodiment assumes that further separations are required, and that the molecules follow the channel 1508, microvalve 1532 being open, and microvalves 1533, 1534 being closed. Optionally some or all of the molecules can be directed into other channels by microvalves 1532, 1533, and 1534 for additional processing as may be desired.

The molecules are guided into channel 1542, where isoelectric focusing is accomplished in a second dimension under an electric field that is established between electrodes 1541, 1543, sink 1527 being suitably opened by a controlling microvalve 1538. A plurality of channels 1556 are distributed along the course of channel 1542 such that molecular species of interest are isoelectrically focused at junctions thereof.

Now yet another electrokinetic axis is established between electrodes 1551, 1553. Microvalve 1538 is closed. A series of microvalves 1555, 1557 disposed on channels 1556 are opened, and the molecular species migrate in parallel through the channels 1556 in a third dimension, a reservoir 1540 being opened by microvalve 1539 to assist the passage. The molecular species eventually reach channel 1547, at which time microvalves 1557 are closed. Microvalve 1568 is opened for reservoir 1566. The species then migrate through a second laser detector 1554, which is of the same type as the first laser detector 1520. The effluent is carried into a sink 1528. It will be evident to those skilled into the art that the system 1500 is quite versatile, and can be extended and tailored to perform sequential separations in many dimensions, some of which could be in accordance with the other techniques taught herein, such as molecular sieving according to the embodiments of FIGS. 11 and 12. Molecular manipulations, such as binding, reaction with enzymes, probes, and other techniques such as are known to the art, can be conducted in lithographically created reaction chambers in a two-dimensional planar substrate intermediate sequential separations. The system can be highly miniaturized and adapted to operate with very small samples.

While this invention has been explained with reference to the structure disclosed herein, it is not confined to the details set forth and this application is intended to cover any modifications and changes as may come within the scope of the following claims:

What is claimed is:

1. An apparatus for the identification of a molecular species in a fluid comprising:

a first laser having a plurality of reflective surfaces and a laser material disposed between said reflective surfaces, whereby the passage of photonic energy through said laser material causes said first laser to produce a coherent output;

a sample chamber disposed between said laser material and said reflective surfaces and being traversed by said photonic energy, said chamber having an inlet for receiving a fluid and an outlet for discharging effluent; and detecting means for detecting changes in the frequency of said coherent output resulting from the presence of said molecular species in said sample chamber.

2. The apparatus according to claim 1, wherein said first laser is a solid state microlaser.

3. The apparatus according to claim 1, wherein said detecting means comprises:

a second laser for generating a coherent reference output; and heterodyning means coupled to said first laser and said second laser for producing a signal representative of a frequency difference between said coherent output of said first laser and said coherent reference output of said second laser.

4. The apparatus according to claim 1, wherein the fluid is an aqueous solution.

5. The apparatus according to claim 1, wherein said sample chamber is disposed adjacent to one of said reflective surfaces.

6. The apparatus according to claim 1, further including coating means comprising an affinity ligand disposed on an interior surface of said sample chamber which binds with said molecular species.

7. The apparatus according to claim 6, further comprising a microlens disposed in said first laser for concentrating photonic energy onto a region of said sample chamber, said coating means being disposed substantially on said region.

8. A system for the identification of a molecular species in a fluid, comprising:

means for separating a molecular species of interest from another molecular species;

a first laser having a plurality of reflective surfaces and a laser material disposed between said reflective surfaces, and having photonic energy traveling through said laser material to produce a coherent output;

a sample chamber disposed between said reflective surfaces and being traversed by said photonic energy, said chamber having an inlet connected to said means for separating, and an outlet for discharging effluent; whereby said output undergoes a frequency shift when said molecular species of interest enters said sample chamber; and detecting means responsive to the frequency of said coherent output for generating an output signal that varies in accordance with the quantity of said molecular species of interest.

9. The apparatus according to claim 8, wherein said first laser is a solid state microlaser.

10. The apparatus according to claim 8, further including coating means comprising an affinity ligand disposed on an interior surface of said sample chamber which binds with said molecular species of interest.

11. The system according to claim 8, wherein said means for separating comprises a molecular sieve comprising a plurality of nanostructures, said nanostructures comprising spaced apart posts defining channels therebetween for passage therethrough of molecules.

12. The system according to claim 11, wherein said nanostructures are fabricated on a planar substrate, and further comprising a cover plate that forms a roof over said channels.

13. The system according to claim 11, wherein said molecular sieve has a pore size of 0.5–0.02 μm.

14. The system according to claim 8, further comprising means for recording said signal of said heterodyning means as a function of time, whereby an interval that is initiated by an introduction of a molecular species into said means for separating and is terminated by a presence of the molecular species in said sample chamber can be measured.

15. A system for the analysis of chromosomes of the type that accepts chromosomes that have been isolated from a cell, comprising:

a network of electroosmotic channels formed on a planar, two-dimensional substrate having an inlet for receiving chromosomes in a fluid environment;

control means for directing the chromosomes along a desired path through said network, whereby a first chromosomal species can be separated from a second chromosomal species;

a first laser having a plurality of reflective optical surfaces and a laser material disposed between said reflective surfaces, and having photonic energy traveling through said laser material for interaction therewith to produce a coherent output;

a sample chamber disposed between said reflective surfaces and being traversed by said photonic energy, said chamber having an inlet connected to said network, and an outlet for discharging effluent; whereby said coherent output undergoes a frequency shift when said chromosomes enter and leave said sample chamber; and detecting means responsive to the frequency of said coherent output for generating an output signal that varies as said chromosomes enter and leave said sample chamber.

16. The apparatus according to claim 15, wherein said first laser is a solid state microlaser.

17. The system according to claim 15, wherein said network comprises:

a plurality of spaced apart posts defining a plurality of intersecting channels therebetween, said channels having a width dimension between about 10 microns and 50 microns;

a first electrode disposed at a first intersection of said channels, wherein said first electrode has a first electrical potential;

a second electrode disposed at a second intersection of said channels, wherein said second electrode has a second electrical potential; and means for controlling the magnitude of said first electrical potential and said second electrical potential;

whereby said chromosomes can be directed from said first intersection to said second intersection by establishing an electrical potential gradient therebetween.

18. The system according to claim 17 wherein said plurality of posts form a diamond array.

19. The system according to claim 15, wherein said network comprises:

a branching network of electroosmotic channels, having a plurality of branch points, each said branch points being guarded by a microvalve that is selectable between an open position and a closed position and each of said branch points having a first arm and a second arm; and means for controlling said microvalves;

whereby said chromosomes can be directed along a selected one of the first arm and the second arm of one of said branch points by controlling said microvalves.

20. The system according to claim 15, further comprising:

a microreaction pulse chamber coupled to said outlet of said sample chamber and having a first chamber for receiving said chromosomes, and a second chamber for containing a reactant for reaction with said first chromosomal species; and means for cyclically deploying said reactant from said second chamber into said first chamber into contact with said first chromosomal species and thereafter returning said reactant into said second chamber.

21. The system according to claim 20, wherein said reactant is attached to a solid support containing a magnetic material therein, and said means for cyclically deploying comprises a pulsed reversible magnetic field generator.

22. The system according to claim 20, wherein said reactant is attached to a solid support material, and said means for cyclically deploying comprises an optical tweezer.

23. The system according to claim 20, wherein said reactant is unbound, and said means for cyclically deploying comprises:

generator means for producing a reversing electroosmotic field in said pulse chamber; and a molecular sieve formed on a two dimensional substrate which allows passage therethrough of said reactant and does not allow passage therethrough of said chromosome.

24. A method for detecting a molecular species using a first laser of the type including first and second reflective surfaces, and a laser medium and sample chamber disposed between said reflective surfaces, said method comprising the steps of:

passing said molecular species through said sample chamber so that the output frequency of said first laser shifts in response to a presence of said molecular species in said sample chamber; and measuring said shift in output frequency.

25. The method according to claim 24, wherein said step of measuring said shift is performed by:

heterodyning said output frequency with an output frequency of a second laser to produce a difference frequency; and measuring said difference frequency.

26. The method according to claim 24, further comprising the step of attaching to a surface of said sample chamber a coating comprising an affinity ligand which binds the molecular species thereto, whereby said output frequency of said first laser varies as the molecular species is bound to said coating.

27. The method according to claim 24, in which said passing step is preceded by the further step of:

passing the molecular species through an electrophoretic or electroosmotic separation system.

28. The method according to claim 27, wherein said separation system comprises a lithographically fabricated molecular sieve.

29. The apparatus of claim 1 in which said changes in the frequency of said coherent output result from the effect which said molecular species have on the index of refraction of said fluid.

30. The apparatus of claim 1 in which said changes in the frequency of said coherent output result from the effect which said molecular species have on the effective dimensions of said sample chamber.

31. The apparatus of claim 8 in which said detecting means includes:

a second laser for producing a coherent reference output; and heterodyning means coupled to said first laser and said second laser for generating as said output signal a signal that varies with the frequency difference between the coherent output of said first laser and the coherent reference output of said second laser.

32. The apparatus of claim 15 in which said detecting means includes:

a second laser for producing a coherent reference output; and heterodyning means coupled to said first laser and said second laser for generating as said output signal a signal that varies with the frequency difference between the coherent output of said first laser and the coherent reference output of said second laser.

* * * * *